US010902594B2

United States Patent
Yamamoto et al.

(10) Patent No.: US 10,902,594 B2
(45) Date of Patent: Jan. 26, 2021

(54) MEDICAL X-RAY IMAGE PROCESSING APPARATUS AND X-RAY IMAGING APPARATUS

(71) Applicant: Shimadzu Corporation, Kyoto (JP)

(72) Inventors: Junya Yamamoto, Kyoto (JP); Takahiro Miyajima, Kyoto (JP); Kazuyoshi Nishino, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/632,172

(22) PCT Filed: Sep. 26, 2017

(86) PCT No.: PCT/JP2017/034801
§ 371 (c)(1),
(2) Date: Jan. 17, 2020

(87) PCT Pub. No.: WO2019/064352
PCT Pub. Date: Apr. 4, 2019

(65) Prior Publication Data
US 2020/0234436 A1   Jul. 23, 2020

(51) Int. Cl.
*G06T 7/00*   (2017.01)
(52) U.S. Cl.
CPC .................... *G06T 7/0012* (2013.01)
(58) Field of Classification Search
CPC ............. G06T 7/0012; G06T 2211/432; G06T 11/006
See application file for complete search history.

(56) References Cited

U.S. PATENT DOCUMENTS

2012/0051498 A1* 3/2012 Koishi ................. G06T 11/006
378/10
2015/0164455 A1* 6/2015 Yamamura ............. A61B 6/025
378/19

FOREIGN PATENT DOCUMENTS

JP   2006-181252 A   7/2006
JP   2016-127870 A   7/2016

OTHER PUBLICATIONS

Written Opinion by the International Search Authority for PCT application PCT/JP2017/034801, dated Dec. 19, 2017, submitted with a machine translation.

* cited by examiner

*Primary Examiner* — Siamak Harandi
(74) *Attorney, Agent, or Firm* — Muir Patent Law, PLLC

(57) ABSTRACT

A medical X-ray image processing apparatus (1) includes a controller (12) configured to acquire positional information of an imaging system (7) based on positional information of positional references (60) and evaluate symmetry of imaging positions of a plurality of X-ray captured images (15) with respect to a reference position (18) on a movement path of the imaging system (7) based on the acquired positional information of the imaging system (7).

11 Claims, 11 Drawing Sheets

FIRST EMBODIMENT

FIRST EMBODIMENT

FIRST EMBODIMENT

FIRST EMBODIMENT

FIG. 5
FIRST EMBODIMENT
(A) X-RAY CAPTURED IMAGE AT FOURTH RELATIVE POSITION
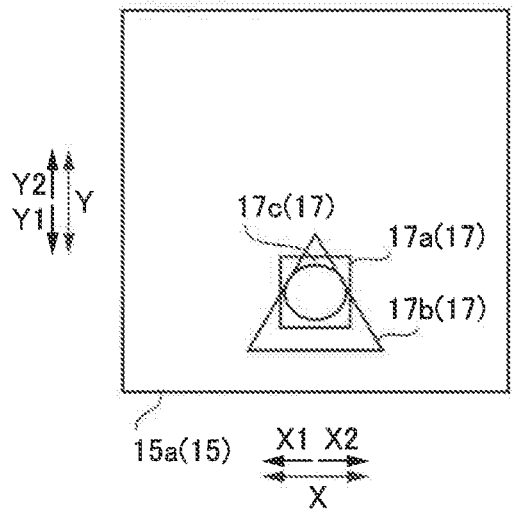
(B) X-RAY CAPTURED IMAGE AT SIXTH RELATIVE POSITION
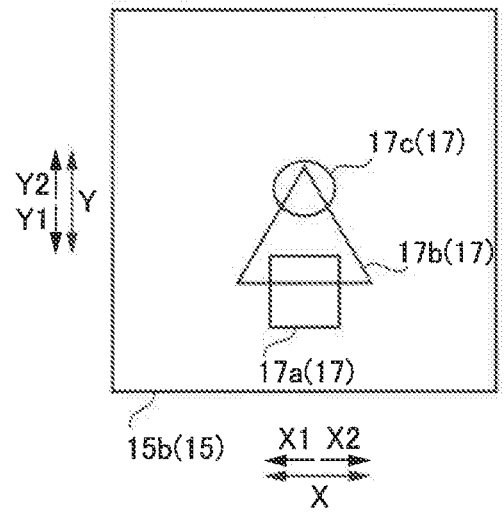
(C) X-RAY CAPTURED IMAGE AT SEVENTH RELATIVE POSITION
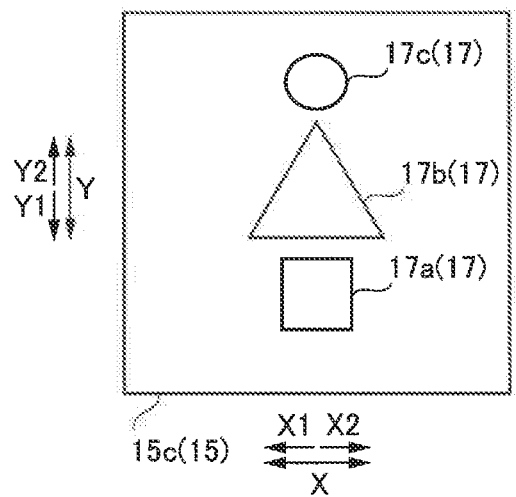
(D) RECONSTRUCTED IMAGE
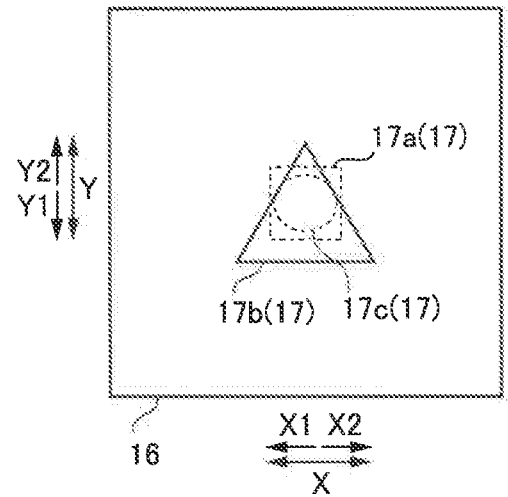

FIRST EMBODIMENT

FIG. 7
FIRST EMBODIMENT (A) POSITIONAL RELATIONSHIP BETWEEN IMAGING SYSTEM AND POSITIONAL REFERENCES

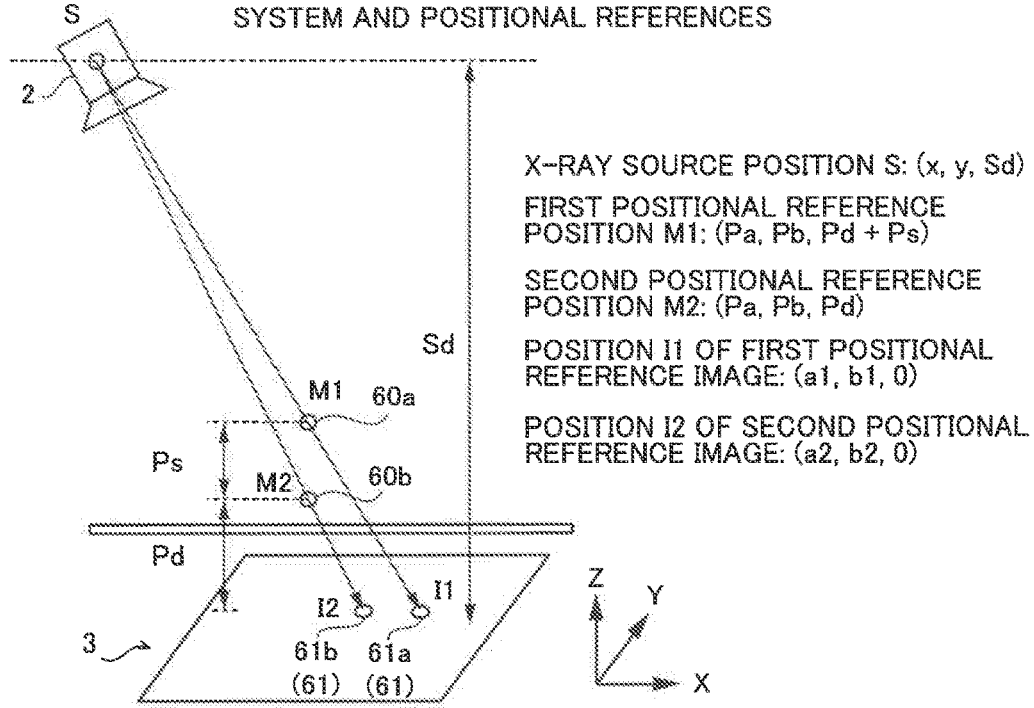

X-RAY SOURCE POSITION S: (x, y, Sd)
FIRST POSITIONAL REFERENCE POSITION M1: (Pa, Pb, Pd + Ps)
SECOND POSITIONAL REFERENCE POSITION M2: (Pa, Pb, Pd)
POSITION I1 OF FIRST POSITIONAL REFERENCE IMAGE: (a1, b1, 0)
POSITION I2 OF SECOND POSITIONAL REFERENCE IMAGE: (a2, b2, 0)

(B) X-RAY CAPTURED IMAGE OF POSITIONAL REFERENCES

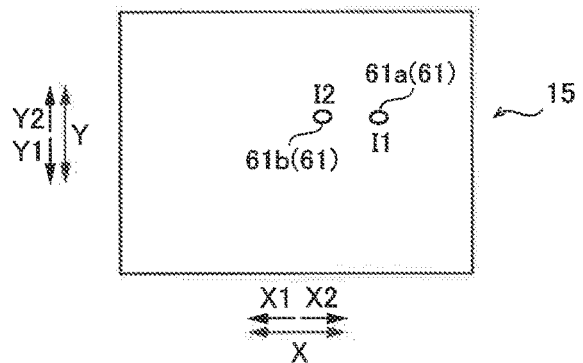

(C) VECTOR DIAGRAMS OF X-RAY SOURCE, POSITIONAL REFERENCES, AND POSITIONAL REFERENCE IMAGES

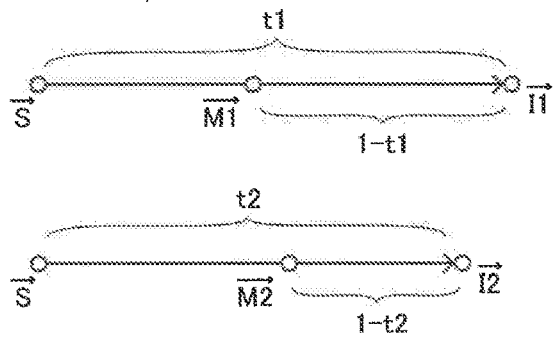

FIRST EMBODIMENT

FIRST EMBODIMENT

SECOND EMBODIMENT

SECOND EMBODIMENT

PROCESSING OF EVALUATING SYMMETRY OF IMAGING POSITIONS

FIRST MODIFIED EXAMPLE OF FIRST EMBODIMENT

MEDICAL X-RAY IMAGE PROCESSING APPARATUS AND X-RAY IMAGING APPARATUS

TECHNICAL FIELD

The present invention relates to a medical X-ray image processing apparatus and an X-ray imaging apparatus, and more particularly, it relates to a medical X-ray image processing apparatus and an X-ray imaging apparatus, each of which reconstructs one image from a plurality of X-ray captured images.

BACKGROUND ART

Conventionally, a medical X-ray image processing apparatus and an X-ray imaging apparatus, each of which reconstructs one image from a plurality of X-ray captured images are known. Such an X-ray imaging apparatus including a medical X-ray image processing apparatus is disclosed in Japanese Patent Laid-Open No. 2006-181252, for example.

In general, in the case in which there is a difference between an assumed imaging position of each image and an actual imaging position of each image due to a mechanical error or the like when one image is reconstructed from a plurality of X-ray captured images, the quality of the image to be obtained may deteriorate if reconstruction is directly performed. Therefore, an X-ray imaging apparatus disclosed in Japanese Patent Laid-Open No. 2006-181252 is configured to acquire positional information of an X-ray source and a detector together when imaging a subject in an X-ray captured image. The X-ray imaging apparatus disclosed in Japanese Patent Laid-Open No. 2006-181252 includes a structure that generates a reconstructed image using an actual accurate imaging position of each captured image acquired when the subject is imaged.

PRIOR ART

Patent Document

Patent Document 1: Japanese Patent Laid-Open No. 2006-181252

SUMMARY OF THE INVENTION

Problems to be Solved by the Invention

Not only when an imaging position of each captured image is not appropriate but also when the relationship between imaging positions of a plurality of captured images is not appropriate, the quality of the generated reconstructed image may deteriorate. In other words, when the imaging positions are not symmetrical, an artifact (virtual image) may be generated in the generated reconstructed image even when the imaging positions are accurate. Therefore, the X-ray imaging apparatus disclosed in Japanese Patent Laid-Open No. 2006-181252 also has a problem that the quality of the generated reconstructed image deteriorates when the imaging positions are not symmetrical.

The present invention is intended to solve the above problem. The present invention aims to provide a medical X-ray image processing apparatus and an X-ray imaging apparatus each capable of evaluating whether or not symmetry between actual imaging positions of a plurality of X-ray captured images is ensured.

Means for Solving the Problems

In order to attain the aforementioned object, a medical X-ray image processing apparatus according to a first aspect of the present invention is used in an X-ray imaging apparatus configured to perform tomosynthesis in which a tomographic image parallel to a moving direction of an imaging system is generated, and includes an image acquirer configured to acquire a plurality of X-ray captured images obtained by X-ray imaging, a positional information acquirer configured to acquire positional information of a plurality of positional references that appear in the plurality of X-ray captured images, a reconstructed image generator configured to generate a reconstructed image obtained by reconstructing the plurality of X-ray captured images into one image, and a controller configured to acquire positional information of the imaging system based on the positional information of the plurality of positional references acquired by the positional information acquirer. The controller is configured to evaluate symmetry of imaging positions of the plurality of X-ray captured images with respect to a reference position on a movement path of the imaging system based on the positional information of the imaging system.

In the medical X-ray image processing apparatus according to the first aspect of the present invention, the controller as described above is provided such that it is possible to evaluate whether or not the symmetry between the actual imaging positions is ensured by evaluating the symmetry of the actual imaging positions of the plurality of X-ray captured images based on the reference position on the movement path of the imaging system. Consequently, an operator can grasp whether or not the actual imaging positions are appropriate. Furthermore, the symmetry of each actual imaging position can be evaluated, and thus when the imaging positions of the plurality of X-ray captured images are inappropriate from the viewpoint of the symmetry of each imaging position, and the quality of the generated reconstructed image is expected to deteriorate, for example, generation of the reconstructed image can be significantly reduced or prevented.

In the aforementioned medical X-ray image processing apparatus according to the first aspect, the controller is preferably configured to evaluate whether or not the reconstructed image is generated based on the symmetry of the imaging positions of the plurality of X-ray captured images. Accordingly, when the symmetry of the imaging positions of the plurality of X-ray captured images is inappropriate, generation of the reconstructed image can be significantly reduced or prevented. Consequently, generation of the reconstructed image with low quality can be significantly reduced or prevented.

In the aforementioned medical X-ray image processing apparatus according to the first aspect, the reconstructed image generator is preferably configured to generate the reconstructed image when the controller determines that the symmetry of the imaging positions of the plurality of X-ray captured images is appropriate, and the controller is preferably configured to give a notification for prompting recapture of an X-ray captured image captured at an inappropriate position when determining that the symmetry of the imaging positions of the plurality of X-ray captured images is inappropriate. Accordingly, when the symmetry of the imaging positions is appropriate, the reconstructed image can be generated without image recapture. When the symmetry of the imaging positions is inappropriate, a notification for prompting image recapture is given, and thus the operator can grasp the necessity of image recapture. That is, based on the symmetry of the imaging positions, the quality of the generated reconstructed image can be predicted in advance, and it can be evaluated whether or not image recapture is necessary.

In the aforementioned medical X-ray image processing apparatus according to the first aspect, the positional information acquirer is preferably configured to acquire the positional information of the plurality of positional references in the X-ray captured images, the plurality of positional references being provided in a phantom arranged in such a manner that the phantom together with a region of interest of a subject appears in each of the X-ray captured images. Accordingly, the phantom is arranged and imaged in such a manner that the phantom together with the region of interest of the subject appears in each of the X-ray captured images such that the positional references can easily appear in the X-ray captured images. Consequently, the degree of freedom of the imaging positions can be improved as compared with the case in which the positional references are fixedly arranged.

In the aforementioned medical X-ray image processing apparatus according to the first aspect, the controller is preferably configured to set a virtual center that is a front position of a region of interest of a subject on the movement path and evaluate the symmetry of the imaging positions using the virtual center, which has been set, as a reference when evaluating the symmetry of the imaging positions of the plurality of X-ray captured images. Accordingly, the virtual center can be easily set at the front position of the region of interest of the subject. Consequently, the symmetry of the plurality of imaging positions with respect to the region of interest can be evaluated using the virtual center as a reference. The front position of the region of interest of the subject refers to a position at which the X-ray source and the region of interest of the subject face each other when the X-ray irradiation direction is set in the normal direction of the movement path of the imaging system.

In this case, the controller is preferably configured to set the virtual center at least upon receiving an operator's setting operation or based on each of the imaging positions and the region of interest of the subject. Accordingly, the virtual center can be easily set.

In the aforementioned medical X-ray image processing apparatus according to the first aspect, the controller is preferably configured to evaluate the symmetry of the imaging positions of the plurality of X-ray captured images by evaluating whether or not the imaging system is arranged at each of a plurality of virtual imaging positions set symmetrically based on the virtual center. Accordingly, the symmetry of each imaging position can be evaluated by comparing the imaging positions with the plurality of symmetrically set virtual imaging positions, respectively. Consequently, as compared with the case in which the symmetry of the imaging positions is evaluated based on relative positions between the imaging positions, the actual imaging positions are respectively compared with the virtual imaging positions corresponding to the imaging positions such that the symmetry can be evaluated, and thus the symmetry of each imaging position can be more easily evaluated.

In the aforementioned medical X-ray image processing apparatus according to the first aspect, the controller is preferably configured to output a display screen showing the imaging positions of the plurality of X-ray captured images. Accordingly, the display screen output from the medical X-ray image processing apparatus is displayed on a display or the like such that the operator can grasp each imaging position. Consequently, the operator can visually grasp the symmetry of each imaging position.

In this case, the controller is preferably configured to display, on the display screen, information of the imaging positions at which the symmetry of the imaging positions of the plurality of X-ray captured images is appropriate when the symmetry is inappropriate. Accordingly, the operator can grasp the positions at which the symmetry is appropriate. Consequently, it is possible to easily reperform imaging at an appropriate (symmetrical) imaging position by perform imaging based on the information of the imaging positions displayed on the display screen.

In the aforementioned medical X-ray image processing apparatus according to the first aspect, the imaging system preferably includes an X-ray source, a detector, and an imaging system position changing mechanism configured to change a relative position between the X-ray source and the detector, and the controller is preferably configured to acquire positional information of the X-ray source based on a distance from the X-ray source to the detector, distances of the plurality of positional references from the detector, and the positional information of the plurality of positional references in the plurality of X-ray captured images. The distance from the X-ray source to the detector and the distances of the plurality of positional references from the detector are known numerical values. Therefore, with the aforementioned configuration, the position of the X-ray source can be acquired by acquiring the positional information of the plurality of positional references in the plurality of X-ray captured images. Consequently, the position of the X-ray source can be acquired from the X-ray captured images without providing a camera or the like configured to acquire the position of the X-ray source, and thus an increase in the number of components can be significantly reduced or prevented.

An X-ray imaging apparatus according to a second aspect of the present invention includes an X-ray source, a detector configured to detect X-rays radiated from the X-ray source, an image processor configured to generate an X-ray captured image from an X-ray intensity distribution detected by the detector, and an imaging system position changing mechanism configured to change a relative position of an imaging system including the X-ray source and the detector. The image processor is configured to acquire positional information of a plurality of positional references that appear in a plurality of X-ray captured images, acquire positional information of the imaging system based on the positional information of the plurality of positional references, and evaluate symmetry of imaging positions of the plurality of X-ray captured images with respect to a reference position on a movement path of the imaging system based on the positional information of the imaging system.

As described above, the X-ray imaging apparatus according to the second aspect of the present invention includes the image processor configured to acquire the positional information of the imaging system and evaluate the symmetry of the imaging positions of the plurality of X-ray captured images with respect to the reference position on the movement path of the imaging system based on the positional information of the imaging system. Accordingly, it is possible to evaluate whether or not the symmetry between the actual imaging positions is ensured by evaluating the symmetry of the imaging positions of the plurality of X-ray captured images. Consequently, it is possible to provide the X-ray imaging apparatus configured to be able to generate a reconstructed image without reperforming imaging when the actual imaging positions are appropriate. In addition, it is possible to provide the X-ray imaging apparatus configured to be able to significantly reduce or prevent generation of the reconstructed image when the imaging positions of the plurality of X-ray captured images are inappropriate from the viewpoint of the symmetry of each imaging position and the quality of the generated reconstructed image is expected to deteriorate.

Effect of the Invention

According to the present invention, as described above, it is possible to provide the medical X-ray image processing apparatus and the X-ray imaging apparatus each capable of evaluating whether or not the symmetry between the actual imaging positions of the plurality of X-ray captured images is ensured.

BRIEF DESCRIPTION OF THE DRAWINGS

FIGS. 5(A) to 5(C) are schematic views of a captured image for illustrating a method for generating the reconstructed image in the medical X-ray image processing apparatus according to the first embodiment of the present invention, and FIG. 5(D) is a schematic view of the reconstructed image.

FIGS. 7(A) to 7(C) are schematic views for illustrating processing of acquiring the position of an X-ray source in the medical X-ray image processing apparatus according to the first embodiment of the present invention.

MODES FOR CARRYING OUT THE INVENTION

Embodiments embodying the present invention are hereinafter described on the basis of the drawings.

First Embodiment

The configuration of an X-ray imaging apparatus 100 including a medical X-ray image processing apparatus 1 according to a first embodiment of the present invention is described with reference to FIGS. 1 to 10.

(Configuration of X-Ray Imaging Apparatus)

The configuration of the X-ray imaging apparatus 100 including the medical X-ray image processing apparatus 1 according to the first embodiment is now described with reference to FIGS. 1 and 2.

Figure 1:
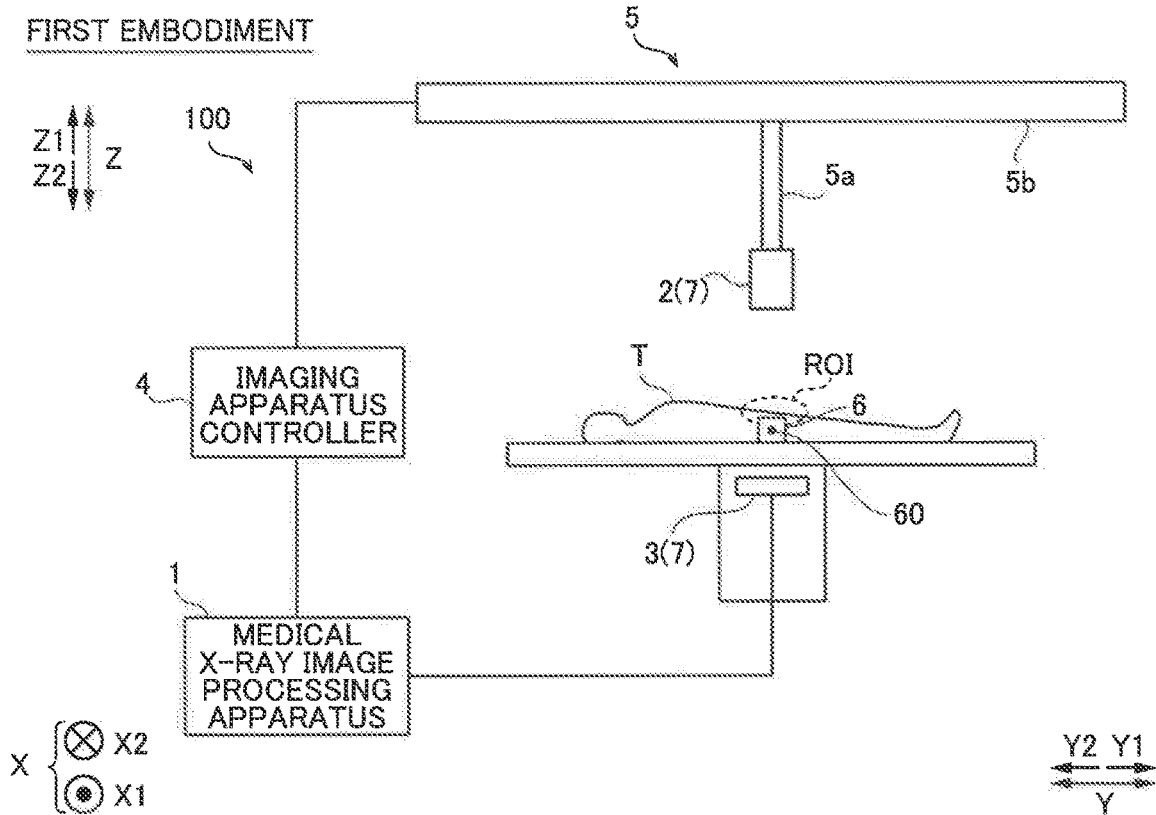
FIG. 1 is a schematic view showing the overall configuration of an X-ray imaging apparatus including a medical X-ray image processing apparatus according to a first embodiment of the present invention.

FIG. 1 is a schematic view of the X-ray imaging apparatus 100 viewed in an X direction. As shown in FIG. 1, the X-ray imaging apparatus 100 includes an X-ray source 2, a detector 3, an imaging apparatus controller 4, an imaging system position changing mechanism 5, and the medical X-ray image processing apparatus 1. In this specification, a direction from the imaging system position changing mechanism 5 (X-ray source mover 5b) toward the detector 3 is defined as a Z2 direction, and the opposite direction is defined as a Z1 direction. Furthermore, a left-right direction in a plane orthogonal to a Z direction is defined as the X direction, a direction toward the rear side of the plane of FIG. 1 is defined as an X2 direction, and a direction toward the front side of the plane of FIG. 1 is defined as an X1 direction. In addition, an upward-downward direction in the plane orthogonal to the Z direction is defined as a Y direction, an upward direction is defined as a Y1 direction, and a downward direction is defined as a Y2 direction.

The X-ray source 2 generates X-rays when a high voltage is applied thereto. The X-ray source 2 is configured to radiate the generated X-rays toward the detector 3.

The detector 3 is configured to detect the X-rays, convert the detected X-rays into electric signals, and read the converted electric signals as image signals. The detector 3 is a flat panel detector (FPD), for example. The detector 3 includes a plurality of conversion elements (not shown) and pixel electrodes (not shown) arranged on the plurality of conversion elements. The plurality of conversion elements and the pixel electrodes are arranged in the detector 3 in such a manner that the arrangement direction of the pixels coincides with the Y direction and the X direction at a predetermined cycle (pixel pitch). The detector 3 is configured to output the acquired image signals to the medical X-ray image processing apparatus 1.

The medical X-ray image processing apparatus 1 is configured to generate X-ray captured images 15 (see FIG. 4) based on the image signals output from the detector 3. In addition, the medical X-ray image processing apparatus 1 is configured to acquire positional information of positional references 60 (see FIG. 6) that appear in a plurality of X-ray captured images 15. The medical X-ray image processing apparatus 1 is configured to acquire positional information of an imaging system 7 based on the positional information of a plurality of positional references 60. The medical X-ray image processing apparatus 1 is configured to evaluate the symmetry of imaging positions of the plurality of X-ray captured images 15 with respect to a reference position 18 (see FIG. 8) on a movement path SP of the imaging system 7 based on the positional information of the imaging system 7. The medical X-ray image processing apparatus 1 is configured to generate a reconstructed image 16 (see FIG. 4) obtained by reconstructing the plurality of X-ray captured images 15 into one image. The imaging system 7 includes the X-ray source 2, the detector 3, and the imaging system position changing mechanism 5 that changes a relative position between the X-ray source 2 and the detector 3.

The medical X-ray image processing apparatus 1 includes a processor such as a central processing unit (CPU), a graphics processing unit (GPU), or a field-programmable gate array (FPGA) configured for image processing. The configuration of the medical X-ray image processing apparatus 1 that evaluates the symmetry of the imaging positions of the plurality of X-ray captured images 15 and the configuration of the medical X-ray image processing apparatus 1 that generates the reconstructed image 16 are described below in detail. The medical X-ray image processing apparatus 1 is an example of an "image processor" in the claims.

The imaging apparatus controller 4 is configured to perform X-ray imaging by irradiating X-rays from the X-ray source 2 toward the detector 3. The imaging apparatus controller 4 is configured to change the relative position of the imaging system 7 with respect to a subject T by moving the X-ray source 2 via the imaging system position changing mechanism 5. The imaging apparatus controller 4 includes a processor such as a CPU.

The imaging system position changing mechanism 5 is configured to change the relative position of the imaging system 7 including the X-ray source 2 and the detector 3 and the angle of the X-ray source 2 based on signals from the imaging apparatus controller 4. The imaging system position changing mechanism 5 includes an X-ray source holder 5a that rotatably holds the X-ray source 2. The imaging system position changing mechanism 5 includes the X-ray source mover 5b that moves the X-ray source holder 5a in the Y direction. The X-ray source holder 5a includes one end rotatably holding the X-ray source 2 and the other end movably held by the X-ray source mover 5b. The X-ray source holder 5a is configured to be able to rotate the X-ray source 2 around an axis in the X direction at one end. That is, the X-ray source holder 5a is configured to be able to change the irradiation angle of the X-ray source 2 based on a signal from the imaging apparatus controller 4. Furthermore, the X-ray source holder 5a is configured to be extendable and contractible in the Z direction. Therefore, the X-ray source holder 5a is configured to be able to change the position of the X-ray source 2 in the Z direction. The X-ray source holder 5a includes a stepping motor, an encoder, etc., for example. Therefore, the X-ray source holder 5a can acquire the position and orientation of the X-ray source 2. The X-ray source mover 5b is configured to move the X-ray source holder 5a in the Y direction based on a signal from the imaging apparatus controller 4. The X-ray source mover 5b includes a motor etc., for example.

The X-ray imaging apparatus 100 is configured to generate the plurality of X-ray captured images 15 by performing imaging while changing the relative position of the imaging system 7 via the imaging system position changing mechanism 5. The relative position of the imaging system 7 includes the position of the X-ray source 2 and the X-ray irradiation angle of the X-ray source 2 with respect to the detector 3.

(Configuration of Medical X-ray Image Processing Apparatus)

Figure 2:
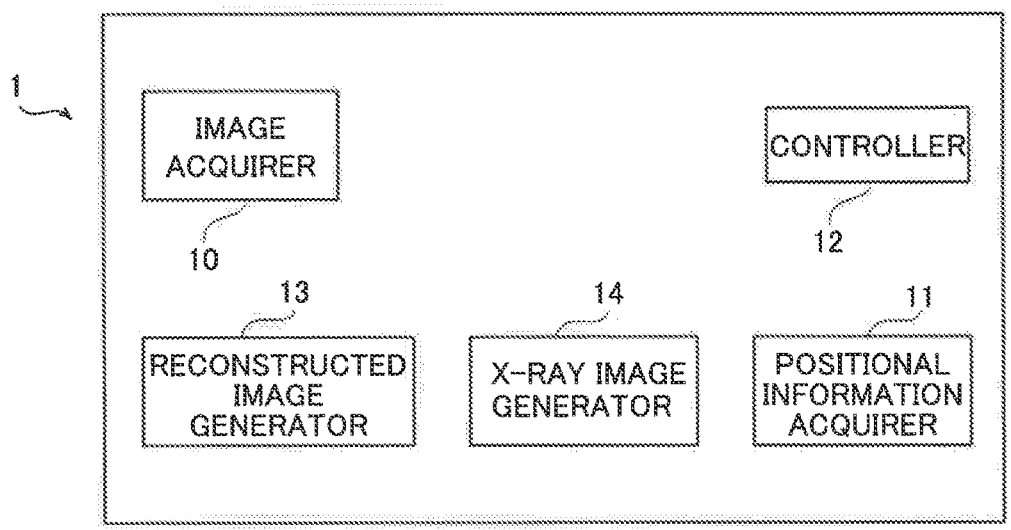
FIG. 2 is a block diagram showing the overall configuration of the medical X-ray image processing apparatus according to the first embodiment of the present invention.

FIG. 2 is a block diagram showing the overall configuration of the medical X-ray image processing apparatus 1. As shown in FIG. 2, the medical X-ray image processing apparatus 1 includes an image acquirer 10, a positional information acquirer 11, a controller 12, a reconstructed image generator 13, and an X-ray captured image generator 14. The image acquirer 10, the positional information acquirer 11, the controller 12, the reconstructed image generator 13, and the X-ray captured image generator 14 are configured as a processing module (processing processor) in the processor such as the FPGA of the medical X-ray image processing apparatus 1.

The image acquirer 10 is configured to acquire the plurality of X-ray captured images 15 obtained by X-ray imaging by the X-ray imaging apparatus 100. Specifically, the image acquirer 10 is configured to acquire the image signals detected by the detector 3. The image acquirer 10 is configured to output the acquired image signals to the X-ray captured image generator 14.

The X-ray captured image generator 14 is configured to generate the X-ray captured images 15 based on the image signals output from the image acquirer 10. The X-ray captured image generator 14 is configured to perform known correction processing associated with imaging of the X-ray captured images 15.

The positional information acquirer 11 is configured to acquire the positional information in the X-ray captured images 15 of the plurality of positional references 60 provided in the phantom 6 arranged in such a manner that the phantom 6 together with a region of interest ROI of the subject T appears in each of the X-ray captured images. In the first embodiment, the positional information acquirer 11 is configured to acquire the positional information of the positional references 60 by image recognition processing.

The controller 12 is configured to evaluate the symmetry of the imaging positions of the plurality of X-ray captured images 15 with respect to the reference position 18 (see FIG. 8) on the movement path SP (see FIG. 8) of the imaging system 7 based on the positional information of the positional references 60 in each of the plurality of X-ray captured images 15. Furthermore, the controller 12 is configured to evaluate whether or not to generate the reconstructed image 16 based on the symmetry of the imaging positions of the plurality of X-ray captured images 15. The controller 12 is configured to set a virtual center 18 that is the front position of the region of interest ROI of the subject T on the movement path SP and evaluate the symmetry of a plurality of imaging positions using the set virtual center 18 as a reference when evaluating the symmetry of the imaging positions of the plurality of X-ray captured images 15. The controller 12 is configured to set the virtual center 18 based on each imaging position and the region of interest ROI of the subject T. The controller 12 is configured to acquire positional information of the X-ray source 2 based on a distances Sd (see FIG. 7) from the X-ray source 2 to the detector 3, distances Pd (see FIG. 7) of the plurality of positional references 60 from the detector 3, and the positional information of the plurality of positional references 60 (images 61 (see FIG. 7) of the positional references 60) in the plurality of X-ray captured images 15. The virtual center 18 is an example of a "reference position" in the claims.

The reconstructed image generator 13 is configured to generate the reconstructed image 16 obtained by reconstructing the plurality of X-ray captured images 15 into one image. Specifically, the reconstructed image generator 13 is configured to generate the reconstructed image 16 when the controller 12 determines that the symmetry of the imaging positions of the plurality of X-ray captured images 15 is appropriate.

(Reconstructed Image)

Processing in which the X-ray imaging apparatus 100 according to the first embodiment captures the plurality of X-ray captured images 15 and processing in which the medical X-ray image processing apparatus 1 reconstructs the plurality of X-ray captured images 15 are now described with reference to FIGS. 3 to 5.

Figure 3:
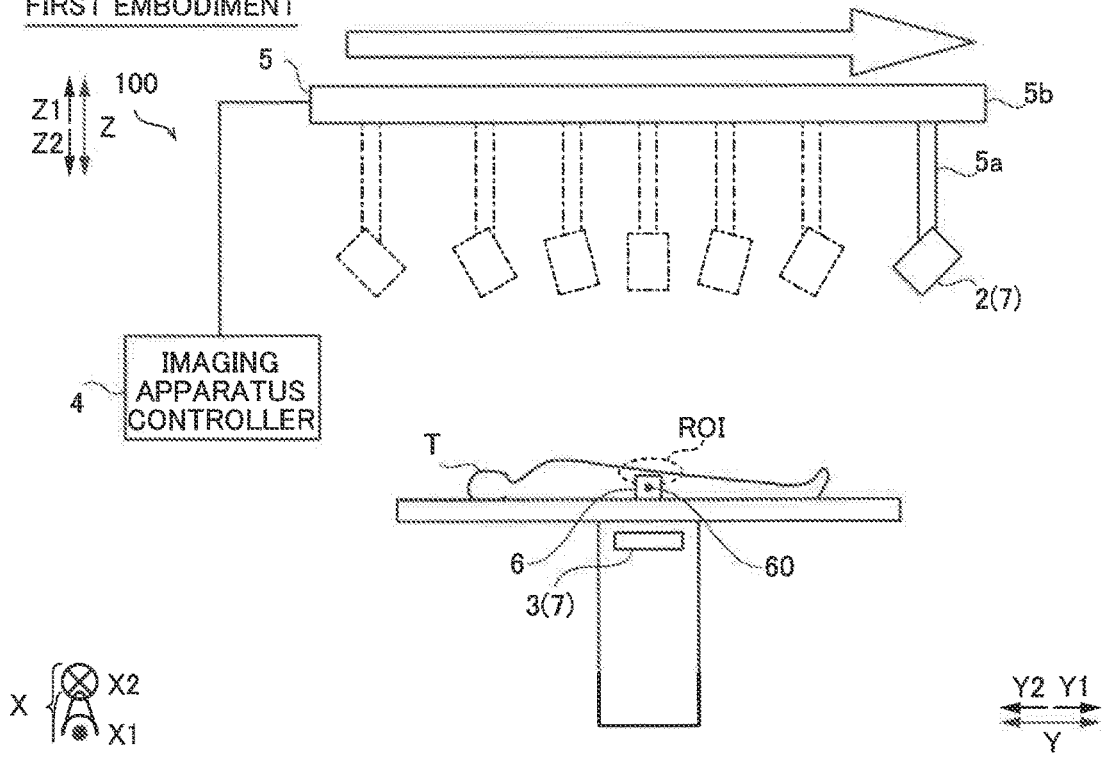
FIG. 3 is a schematic view for illustrating a method for capturing an X-ray captured image in the X-ray imaging apparatus according to the first embodiment of the present invention.

FIG. 3 is a schematic view at the time of capturing the plurality of X-ray captured images 15 by the X-ray imaging apparatus 100 according to the first embodiment. As shown in FIG. 3, in the first embodiment, the X-ray imaging apparatus 100 is configured to perform imaging while causing the imaging system position changing mechanism 5 to change the relative position of the imaging system 7 with respect to the subject T. Specifically, the imaging system position changing mechanism 5 is configured to move the X-ray source 2 in the Y1 direction as it moves. A straight line that connects X-ray sources 2 respectively arranged at relative positions is the movement path SP. The imaging system position changing mechanism 5 is configured to change the X-ray irradiation direction of the X-ray source 2. Thus, imaging is performed while the imaging system position changing mechanism 5 changes the relative position of the imaging system 7 with respect to the subject T. The X-ray imaging apparatus 100 is an apparatus that performs so-called tomosynthesis. Tomosynthesis is an imaging method for generating a tomographic image in an arbitrary height (thickness) direction in a cross-section parallel to the moving direction of the X-ray source 2. In an example shown in FIG. 3, a tomographic image at an arbitrary height in the Z direction is generated in the cross-section of the subject T parallel to the Y direction.

Figure 4:
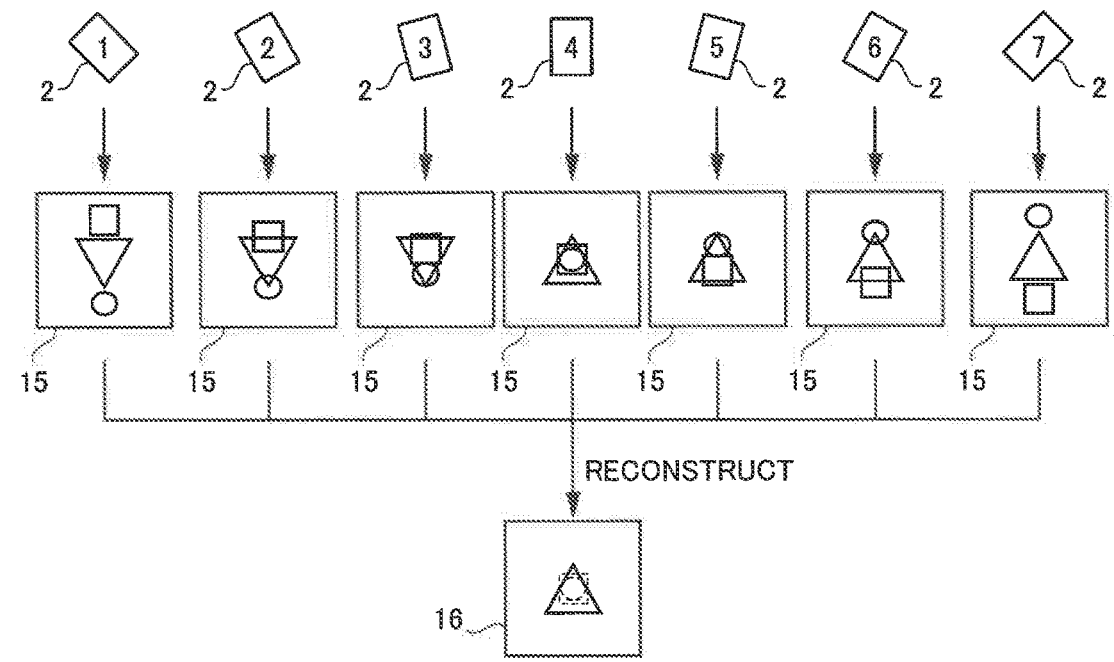
FIG. 4 is a schematic view for illustrating images captured by the X-ray imaging apparatus according to the first embodiment of the present invention and a reconstructed image.

FIG. 4 is a schematic view of the X-ray captured images 15 respectively acquired at the relative positions, and a schematic view of the reconstructed image 16 obtained by reconstructing those images. As shown in FIG. 4, when the imaging system 7 is arranged in different locations, the irradiation angle of an X-ray radiated from the X-ray source 2 to the detector 3 changes, and thus an obtained X-ray captured image 15 also differs. In the first embodiment, the medical X-ray image processing apparatus 1 is configured to generate the reconstructed image 16 by reconstructing the plurality of X-ray captured images with different ways of capturing the subject T into one image. Numerical values shown for the X-ray source 2 in FIG. 4 each represent the relative position of the imaging system 7. That is, the numerical values indicate first to seventh relative positions in order from the left side of FIG. 4.

FIGS. 5(A) to 5(C) are schematic views of X-ray captured images 15 obtained by imaging a region of the subject T including a plurality of internal structures 17a, 17b, and 17c at substantially the same positions in the Y direction and the X direction and at different positions in the Z direction by the X-ray imaging apparatus 100 according to the first embodiment, and FIG. 5(D) is a schematic view of the reconstructed image 16 reconstructed by the medical X-ray image processing apparatus 1. That is, the internal structures 17a to 17c are internal structures 17 at different depth positions (positions in the Z direction) in an arbitrary region of interest ROI.

FIG. 5(A) shows an X-ray captured image 15a captured with the imaging system 7 arranged at the fourth relative position (see FIG. 4). FIG. 5(B) shows an X-ray captured image 15b captured with the imaging system 7 arranged at the second relative position (see FIG. 4). FIG. 5(C) is an X-ray captured image 15c captured with the imaging system 7 arranged at the seventh relative position (see FIG. 4).

In an example shown in FIG. 5(A), the subject T is imaged in the Z2 direction, and thus the internal structures 17a to 17c of the subject T are imaged in an overlapping state. In an example shown in FIG. 5(B), the imaging system 7 is arranged at the second relative position by the imaging system position changing mechanism 5 and captures an image, and thus X-rays are incident on the subject T from an oblique direction. Therefore, the internal structures 17a to 17c are depicted with their positions shifted in the Y2 direction. In the example shown in FIG. 5(B), an angle at which X-rays are radiated is small, and thus the internal structures 17a to 17c are depicted still in an overlapping state. In an example shown in FIG. 5(C), the imaging system 7 is arranged at the seventh relative position by the imaging system position changing mechanism 5 and captures an image, and thus an angle at which X-rays are incident on the subject T becomes larger as compared with the case in which the imaging system 7 is arranged at the second relative position and captures an image. Therefore, in the example shown in FIG. 5(C), the internal structures 17a to 17c are depicted without overlapping with each other. The medical X-ray image processing apparatus 1 generates the reconstructed image 16 by reconstructing these X-ray captured images 15a to 15c. When the reconstructed image 16 is generated, a cross-section of any of the internal structures 17a to 17c at a desired depth position is imaged. Accordingly, the internal structure 17 at the desired depth position can be imaged. An example shown in FIG. 5(D) shows the reconstructed image 16 reconstructed focusing on the internal structure 17b.

In tomosynthesis, imaging is performed while the relative position of the imaging system 7 is changed such that a tomographic image parallel to the moving direction of the imaging system 7 is generated. The imaging system 7 is arranged at a position at which the symmetry of each imaging position is ensured, and each image used to generate a tomographic image is captured. When the symmetry of the imaging position of each image is inappropriate, an artifact (virtual image) may be generated in the reconstructed image 16. Therefore, the controller 12 is configured to evaluate the symmetry of each imaging position. Note that the symmetry of each imaging position is determined depending on whether or not the imaging system 7 is arranged at positions on the movement path SP of the imaging system 7, at which distances to the reference position 18 are the same, or whether or not X-rays are radiated at the same irradiation angle from opposite directions with respect to the reference position 18 on the movement path SP of the imaging system 7.

(Evaluation of Symmetry of Imaging Positions)

Processing in which the medical X-ray image processing apparatus 1 according to the first embodiment evaluates the symmetry of the imaging positions is now described with reference to FIGS. 6 to 9.

When the subject T is imaged by the X-ray imaging apparatus 100, the phantom 6 used as reference for acquiring the positional information of the X-ray source 2 is arranged, and imaging is performed. In the first embodiment, the positional information acquirer 11 is configured to acquire the positional information of the plurality of positional references 60 included in the phantom 6. Furthermore, in the first embodiment, the controller 12 is configured to acquire the positional information of the X-ray source 2 based on the positional information of the positional references 60 and the positional information of the images 61 of the positional references 60 that appear in the X-ray captured image 15. The positional information of the images 61 of the positional references 60 includes coordinate values in X-ray captured image 15. The positional information of the X-ray source 2 includes coordinate values in a XZ plane.

Figure 6:
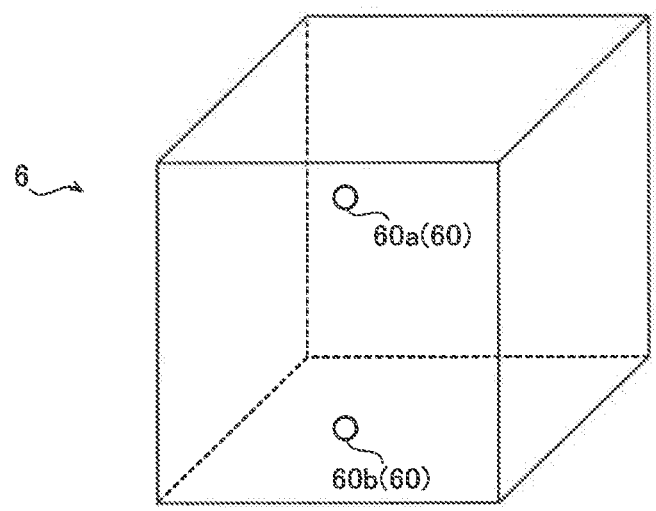
FIG. 6 is a schematic view of a phantom used when the X-ray captured image is captured in the X-ray imaging apparatus according to the first embodiment of the present invention.

FIG. 6 is a schematic view of the phantom 6 used as a reference for acquiring the positional information of the X-ray source 2 in the X-ray imaging apparatus 100 according to the first embodiment. In an example shown in FIG. 6, the phantom 6 is made of resin, for example, and includes the plurality of positional references 60 inside. Specifically, the phantom 6 includes a first positional reference 60a and a second positional reference 60b inside. The first positional reference 60a and the second positional reference 60b each include an X-ray absorber that absorbs X-rays. When the phantom 6 is imaged, the first positional reference 60a and the second positional reference 60b absorb X-rays, and thus the first positional reference 60a and the second positional reference 60b can be detected in the X-ray captured image 15. The positional references 60 may be made of any material as long as the amount of X-ray absorption is large. In the first embodiment, heavy metal, for example, is used as the positional references 60. Examples of the heavy metal include gold, lead, and tungsten. A material for the phantom 6 is not limited to resin. Furthermore, the positional references 60 may not be provided inside the phantom 6. For example, the positional references 60 may be provided on a surface of the phantom 6.

Processing of acquiring the positional information of the X-ray source 2 is now described with reference to FIG. 7. FIG. 7(A) is a schematic view showing the positional relationship between the imaging system 7 and the positional references 60 when imaging is performed with the X-ray source 2 arranged at the first relative position (see FIG. 3). FIG. 7(B) is a schematic view of an X-ray captured image 15 captured with the X-ray source 2 arranged at the first relative position. FIG. 7(C) shows an example in which the positional relationship between the X-ray source 2, the positional references 60, and the images 61 of the positional references 60 in the case of arranging the X-ray source 2 at the first relative position is illustrated by a vector diagram. In FIG. 7(A), the phantom 6 is not shown for convenience.

As shown in FIG. 7(A), when the X-ray source 2 is arranged at a predetermined position (the first relative position, for example) and radiates X-rays from an oblique direction, the X-rays that have passed through the first positional reference 60a and the second positional reference 60b reach points on the detector 3 that have different X coordinates. Therefore, as shown in FIG. 7(B), an image 61a of the first positional reference 60a and an image 61b of the second positional reference 60b are arranged at the same X coordinate and Y coordinate and different Z coordinates. In an example shown in FIG. 7(B), the image 61a of the first positional reference 60a and the image 61b of the second positional reference 60b are depicted at different positions in the X direction in the X-ray captured image 15. When S represents the position of the X-ray source 2, M1 represents the position of the first positional reference 60a, M2 represents the position of the second positional reference 60b, I1 represents the position of the image 61a of the first positional reference 60a, and I2 represents the position of the image 61b of the second positional reference 60b, the vector diagram as shown in FIG. 7(C) can be obtained. As shown in FIG. 7(C), the X-ray source 2, the positional references 60, and the images 61 of the positional references 60 have a relationship of externally dividing points. That is, the image 61a of the first positional reference 60a is a point that externally divides a line segment SM1 including the X-ray source 2 and the first positional reference 60a at a ratio of t1:(1−t1). The image 61b of the second positional reference 60b is a point that externally divides a line segment SM2 including the X-ray source 2 and the second positional reference 60b at a ratio of t2:(1−t2). From the above relationship, the following formulas (1) and (2) are obtained.

[Formula 1]

$$\vec{S}*t1 + \vec{M1}*(1-t1) = \vec{I}1 \tag{1}$$

$$\vec{S}*t2 + \vec{M2}*(1-t2) = \vec{I}2 \tag{2}$$

The positional coordinates of the position S of the X-ray source 2 are defined as (x, y, Sd). Furthermore, the positional coordinates of the position M1 of the first positional reference 60a are defined as (Pa, Pb, Pd+Ps). In addition, the positional coordinates of the position M2 of the second positional reference 60b are defined as (Pa, Pb, Pd). The positional coordinates of the position I1 of the image 61a of the first positional reference 60a on the detector 3 are defined as (a1, b1, 0). The positional coordinates of the position I2 of the image 61b of the second positional reference 60b on the detector 3 are defined as (a2, b2, 0). Note that x is the coordinate of the X-ray source 2 in the X direction. Furthermore, y is the coordinate of the X-ray source 2 in the Y direction. Pa is the coordinates of the first positional reference 60a and the second positional reference 60b in the X direction. Pb is the coordinates of the first positional reference 60a and the second positional reference 60b in the Y direction. Sd is a distance from the detector 3 to the X-ray source 2 (SID: source image receptor distance) in the Z direction. Pd is a distance from the detector 3 to the second positional reference 60b in the Z direction. Ps is a distance between the first positional reference 60a and the second positional reference 60b in the Z direction.

From the positional coordinates of the X-ray source 2, the positional coordinates of the first positional reference 60a, the positional coordinates of the second positional reference 60b, the positional coordinates of the image 61a of the first positional reference 60a, the positional coordinates of the image 61b of the second positional reference 60b, and the above formulas (1) and (2), the following formulas (3) to (8) are obtained.

[Formula 2]

$$x*t1 + Pa*(1-t1) = a1 \tag{3}$$

$$x*t2 + Pa*(1-t2) = a2 \tag{4}$$

$$y*t1 + Pa*(1-t1) = b1 \tag{5}$$

$$y*t2 + Pa*(1-t2) = b2 \tag{6}$$

$$Sd*t1 + (Pd+Ps)*(1-t1) = 0 \tag{7}$$

$$Sd*t2 + Pd*(1-t2) = 0 \tag{8}$$

In the above formulas (3) to (8), Sd, Pd, and Ps are known values, and thus the number of unknowns and the number of formulas are equal, and the positional information of the X-ray source 2 can be acquired. Specifically, the following formulas (9) and (10) are obtained from the formulas (7) and (8).

[Formula 3]

$$t1 = \frac{Pd + Ps}{Pd + Ps - Sd} \quad (9)$$

$$t2 = \frac{Pd}{Pd - Sd} \quad (10)$$

When the solution of the above formula (9) is t1=α and the solution of the above formula (10) is t2=β, the following formula (11) is obtained from the above formulas (1) and (2). Moreover, the following formula (12) is obtained from the above formulas (3) and (4).

[Formula 4]

$$x = \frac{a1 * (1 - \beta) - a2 * (1 - \alpha)}{\beta - \alpha} \quad (11)$$

$$y = \frac{b1 * (1 - \beta) - b2 * (1 - \alpha)}{\beta - \alpha} \quad (12)$$

The X coordinate value of the image 61a of the first positional reference 60a and the X coordinate value of the image 61b of the second positional reference 60b in the X-ray captured image 15 are acquired such that a1 and a2 in the above formula (11) are obtained. Furthermore, the Y coordinate value of the image 61a of the first positional reference 60a and the Y coordinate value of the image 61b of the second positional reference 60b in the X-ray captured image 15 are acquired such that b1 and b2 in the above formula (12) are obtained. Therefore, the controller 12 can acquire the positional information of the X-ray source 2 at the time of capturing each image from the coordinate values of the positional references 60 in each image and the above formulas (11) and (12).

Figure 8:
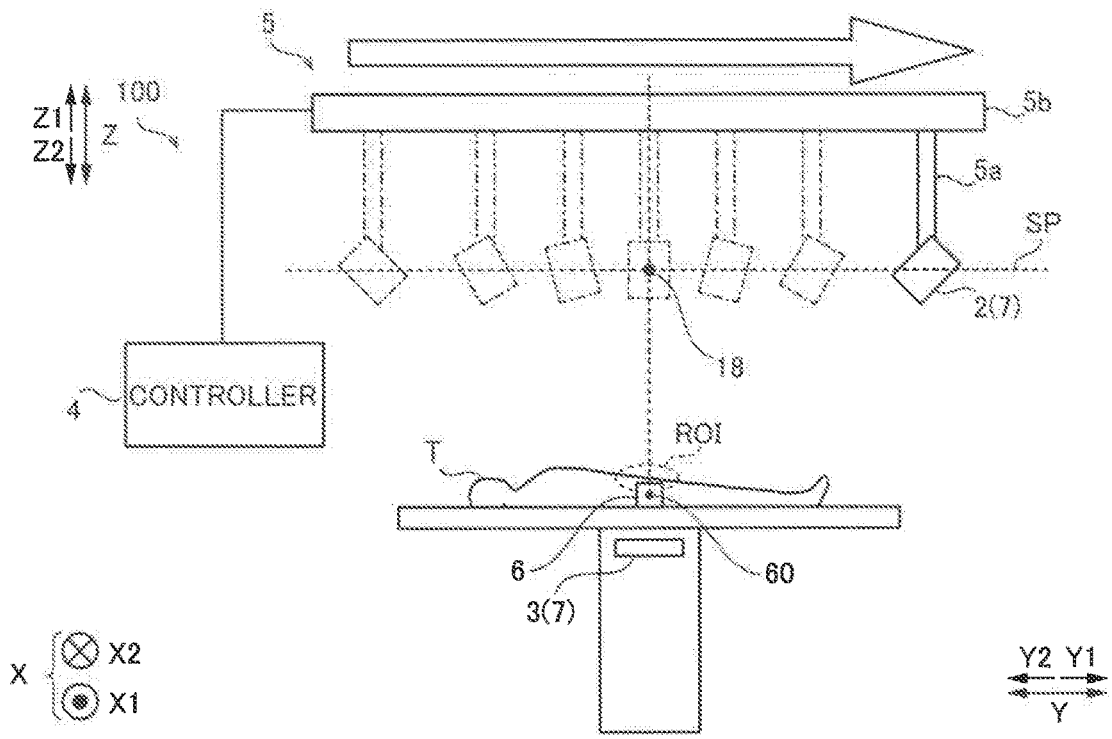
FIG. 8 is a schematic view for illustrating processing of setting a virtual center in the medical X-ray image processing apparatus according to the first embodiment of the present invention.

Processing in which the controller 12 evaluates the symmetry of the imaging positions is now described with reference to FIGS. 8 and 9.

In the first embodiment, the controller 12 is configured to set the virtual center 18 that is the front position of the region of interest ROI of the subject T on the movement path SP and valuate the symmetry of the plurality of imaging positions using the set virtual center 18 as a reference when evaluating the symmetry of the imaging positions of the plurality of X-ray captured images 15. Specifically, the controller 12 is configured to set the virtual center 18 based on each imaging position and the region of interest ROI of the subject T. In an example shown in FIG. 8, the fourth relative position is the front position of the region of interest ROI of the subject T, and thus the controller 12 sets the position of the X-ray source 2 at the fourth relative position as the virtual center 18. The front position of the region of interest ROI of the subject T refers to a position at which the X-ray source 2 and the region of interest ROI of the subject T face each other when the X-ray irradiation direction is set in the normal direction of the movement path SP of the imaging system 7. In the first embodiment, the region of interest ROI of the subject T is set by an operator.

Figure 9:
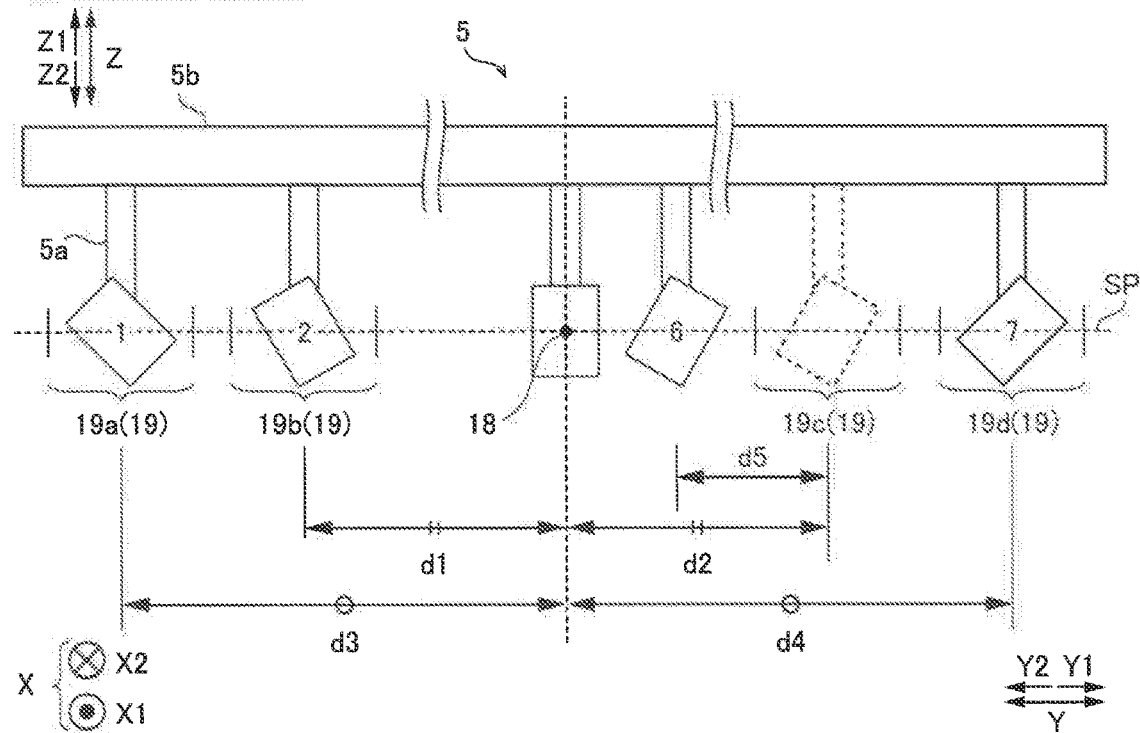
FIG. 9 is a schematic view for illustrating processing of evaluating the symmetry of imaging positions in the medical X-ray image processing apparatus according to first embodiment of the present invention.

FIG. 9 is a schematic view for illustrating processing in which the controller 12 evaluates the symmetry of each imaging position. In FIG. 9, an example is shown in which the symmetry at the first relative position, the second relative position, the sixth relative position, and the seventh relative position is evaluated. In the example shown in FIG. 9, illustration of the X-ray source 2 at the third relative position and the fifth relative position is omitted for convenience.

The controller 12 is configured to evaluate the symmetry of the imaging positions of the plurality of X-ray captured images 15 by evaluating whether or not the imaging system 7 is arranged at each of a plurality of virtual imaging positions 19 set symmetrically based on the virtual center 18. Specifically, the controller 12 sets the virtual imaging positions 19 based on the virtual center 18 and the total number of captured images. In the example shown in FIG. 9, the total number of captured images is seven, and the virtual center 18 is the position of the X-ray source 2 arranged at the fourth relative position, and thus the controller 12 sets the virtual imaging positions 19 at the time of capturing the remaining six images. That is, the controller 12 sets a second virtual imaging position 19b corresponding to the second relative position at a position at a distance d1 from the virtual center 18. In addition, the controller 12 sets a sixth virtual imaging position 19c corresponding to the sixth relative position at a position at a distance d2 from the virtual center 18. The controller 12 sets the distance d1 and the distance d2 to be equal to each other and sets directions from the virtual center 18 to be opposite to each other such that the second relative position and the sixth relative position are symmetrical. Similarly, the controller 12 sets a first virtual imaging position 19a corresponding to the first relative position and a seventh virtual imaging position 19d corresponding to the seventh relative position. The controller 12 sets a distance d3 and a distance d4 to be equal to each other and sets directions from the virtual center 18 to be opposite to each other such that the first relative position and the seventh relative position are also symmetrical. Although not shown, the controller 12 similarly sets a third virtual imaging position and a fifth virtual imaging position corresponding to the third relative position and the fifth relative position.

When the first relative position to the seventh relative position are arranged at the first virtual imaging position 19a to the seventh virtual imaging position 19d, respectively, the controller 12 evaluates that the symmetry of each imaging position is appropriate. FIG. 9 shows an example in which the center of each virtual imaging position 19 and the center of the X-ray source 2 at each relative position substantially coincide, but the center of each virtual imaging position 19 and the center of the X-ray source 2 at each relative position may not substantially coincide. For example, the controller 12 may be configured to set a threshold at each virtual imaging position 19 and evaluate that the X-ray source 2 is disposed symmetrically when the center of the X-ray source 2 is disposed within the threshold range.

In the example shown in FIG. 9, the sixth relative position is shifted from the sixth virtual imaging position 19c by a distance d5 in the Y2 direction, and thus the controller 12 evaluates that the symmetry of each imaging position is inappropriate. In the first embodiment, the controller 12 is configured to give a notification for prompting recapture of the X-ray captured image 15 captured at an inappropriate position when the symmetry of the imaging positions of the plurality of X-ray captured images 15 is inappropriate. Any method may be used as a notification for prompting image recapture. For example, an alert may be issued to notify the operator of image recapture.

(Processing of Evaluating Symmetry of Imaging Positions)

Figure 10:
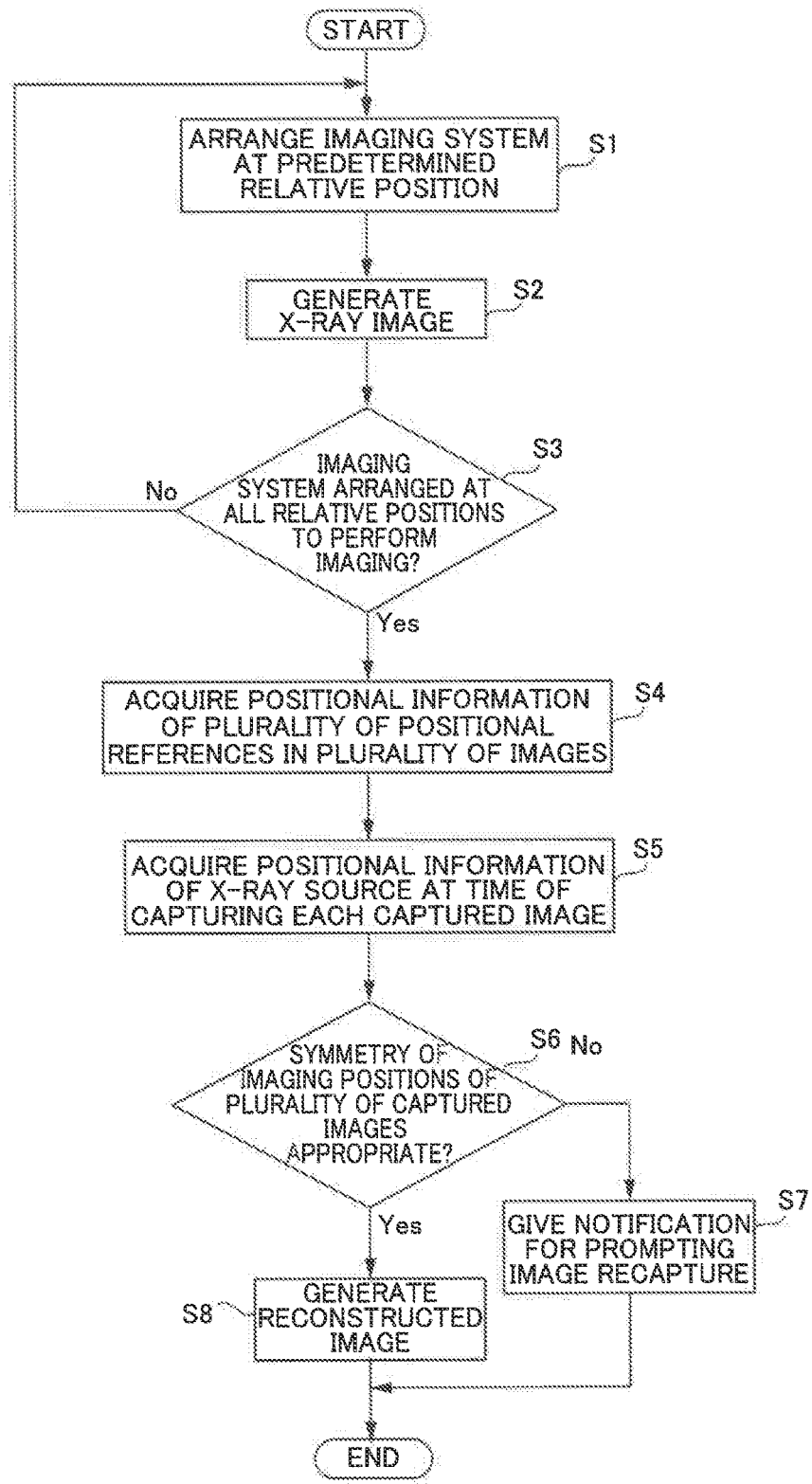
FIG. 10 is a flowchart for illustrating the processing of evaluating the symmetry of the imaging positions in the medical X-ray image processing apparatus according to the first embodiment of the present invention.

A flow of processing in which the medical X-ray image processing apparatus 1 according to the first embodiment evaluates the symmetry of each imaging position is now described with reference to FIG. 10.

In step S1, the imaging apparatus controller 4 arranges the imaging system 7 at a predetermined relative position via the imaging system position changing mechanism 5. Thereafter, in step S2, the X-ray captured image generator 14 generates an X-ray captured image 15.

Then, in step S3, the imaging apparatus controller 4 determines whether or not the imaging system 7 has been arranged at all the relative positions to perform imaging. When the imaging system 7 has been arranged at all the relative positions to perform imaging, the processing advances to step S4. When the imaging system 7 has not been arranged at all the relative positions to perform imaging, the processing returns to step S1. In the example of FIG. 4, all the relative positions indicate seven positions of the first relative position to the seventh relative position.

In step S4, the positional information acquirer 11 acquires the positional information of the first positional reference 60a and the second positional reference 60b that appear in the plurality of X-ray captured images 15. Thereafter, the processing advances to step S5.

In step S5, the controller 12 acquires the positional information of the X-ray source 2 based on the positional information of the first positional reference 60a and the second positional reference 60b in each of the plurality of X-ray captured images 15. Thereafter, the processing advances to step S6.

Then, in step S6, the controller 12 evaluates the symmetry of each imaging position. When the symmetry of each imaging position is appropriate, the processing advances to step S7. When the symmetry of each imaging position is inappropriate, the processing advances to step S8.

In step S7, the reconstructed image generator 13 generates the reconstructed image 16 obtained by reconstructing the plurality of X-ray captured images 15 into one image.

In step S8, the controller 12 gives a notification for prompting recapture of the X-ray captured image 15 captured at an inappropriate position. When a notification for prompting image recapture is given, the operator reperforms imaging, and the reconstructed image 16 is generated.

Advantages of Embodiment

In the embodiment of the present invention, the following advantages are obtained.

In the first embodiment, as described above, the medical X-ray image processing apparatus 1 is used in the X-ray imaging apparatus 100 that performs tomosynthesis in which a tomographic image parallel to the moving direction of the imaging system 7 is generated, and includes the image acquirer 10 configured to acquire the plurality of X-ray captured images 15 obtained by X-ray imaging, the positional information acquirer 11 configured to acquire the positional information of the first positional reference 60a and the second positional reference 60b that appear in the plurality of X-ray captured images, the reconstructed image generator 13 configured to generate the reconstructed image 16 obtained by reconstructing the plurality of X-ray captured images 15 into one image, and the controller 12 configured to acquire the positional information of the imaging system 7 based on the positional information of the first positional reference 60a and the second positional reference 60b acquired by the positional information acquirer 11. The controller 12 is configured to evaluate the symmetry of the imaging positions of the plurality of X-ray captured images 15 with respect to the reference position 18 on the movement path SP of the imaging system 7 based on the positional information of the imaging system 7. Accordingly, it is possible to evaluate whether or not the symmetry between the actual imaging positions is ensured by evaluating the symmetry of the actual imaging positions of the plurality of X-ray captured images 15 based on the reference position 18 on the movement path SP of the imaging system 7. Consequently, the operator can grasp whether or not the actual imaging positions are appropriate. Furthermore, the symmetry of each actual imaging position can be evaluated, and thus when the imaging positions of the plurality of X-ray captured images 15 are inappropriate from the viewpoint of the symmetry of each imaging position, and the quality of the generated reconstructed image 16 is expected to deteriorate, for example, generation of the reconstructed image 16 can be significantly reduced or prevented.

In the first embodiment, as described above, the controller 12 is configured to evaluate whether or not the reconstructed image 16 is generated based on the symmetry of the imaging positions of the plurality of X-ray captured images 15. Accordingly, when the symmetry of the imaging positions of the plurality of X-ray captured images 15 is inappropriate, generation of the reconstructed image 16 can be significantly reduced or prevented. Consequently, generation of the reconstructed image 16 with low quality can be significantly reduced or prevented.

In the first embodiment, as described above, the reconstructed image generator 13 is configured to generate the reconstructed image 16 when the controller 12 determines that the symmetry of the imaging positions of the plurality of X-ray captured images 15 is appropriate, and the controller 12 is configured to give a notification for prompting recapture of the X-ray captured image 15 captured at an inappropriate position when determining that the symmetry of the imaging positions of the plurality of X-ray captured images 15 is inappropriate. Accordingly, when the symmetry of the imaging positions is appropriate, the reconstructed image 16 can be generated without image recapture. When the symmetry of the imaging positions is inappropriate, a notification for prompting image recapture is given, and thus the operator can grasp the necessity of image recapture. That is, based on the symmetry of the imaging positions, the quality of the generated reconstructed image 16 can be predicted in advance, and it can be evaluated whether or not image recapture is necessary.

In the first embodiment, as described above, the positional information acquirer 11 is configured to acquire the positional information in the X-ray captured image 15 of the first positional reference 60a and the second positional reference 60b provided in the phantom 6 arranged in such a manner that the phantom 6 together with the region of interest ROI of the subject T appears in each of the X-ray captured images. Accordingly, the first positional reference 60a and the second positional reference 60b can easily appear in the X-ray captured image 15 by arranging and imaging the phantom 6 in such a manner that the phantom 6 together with the region of interest ROI of the subject T appears in each of the X-ray captured images. Consequently, the degree of freedom of the imaging positions can be improved as compared with the case in which the first positional reference 60a and the second positional reference 60b are fixedly arranged.

In the first embodiment, as described above, the controller 12 is configured to set the virtual center 18 that is the front position of the region of interest ROI of the subject T on the movement path SP and evaluate the symmetry of the plurality of imaging positions using the set virtual center 18 as a reference when evaluating the symmetry of the imaging positions of the plurality of X-ray captured images 15. Accordingly, the virtual center 18 can be easily set at the front position of the region of interest ROI of the subject T. Consequently, the symmetry of the plurality of imaging positions with respect to the region of interest ROI can be evaluated using the virtual center 18 as a reference.

In the first embodiment, as described above, the controller 12 is configured to set the virtual center 18 based on each imaging position and the region of interest ROI of the subject T. Accordingly, the virtual center 18 can be easily set.

In the first embodiment, as described above, the controller 12 is configured to evaluate the symmetry of the imaging positions of the plurality of X-ray captured images 15 by evaluating whether or not the imaging system 7 is arranged at each of the plurality of virtual imaging positions 19 set symmetrically based on the virtual center 18. Accordingly, the symmetry of each imaging position can be evaluated by comparing the imaging positions with the plurality of symmetrically set virtual imaging positions 19, respectively. Consequently, as compared with the case in which the symmetry of the imaging positions is evaluated based on relative positions between the imaging positions, the actual imaging positions are respectively compared with the virtual imaging positions 19 corresponding to the imaging positions such that the symmetry can be evaluated, and thus the symmetry of each imaging position can be more easily evaluated.

In the first embodiment, as described above, the imaging system 7 includes the X-ray source 2, the detector 3, and the imaging system position changing mechanism 5 configured to change the relative position between the X-ray source 2 and the detector 3, and the controller 12 is configured to acquire the positional information of the X-ray source 2 based on the distance Sd from the X-ray source 2 to the detector 3, the distances Pd of the plurality of positional references 60 from the detector 3, and the positional information of the first positional reference 60a and the second positional reference 60b in the plurality of X-ray captured images 15. The distance Sd from the X-ray source 2 to the detector 3 and the distance Pd of the second positional reference 60b from the detector 3 are known numerical values. Therefore, with the aforementioned configuration, the position of the X-ray source 2 can be acquired by acquiring the positional information of the first positional reference 60a and the second positional reference 60b in the plurality of X-ray captured images 15. Consequently, the position of the X-ray source 2 can be acquired from the X-ray captured images 15 without providing a camera or the like configured to acquire the position of the X-ray source 2, and thus an increase in the number of components can be significantly reduced or prevented.

In the first embodiment, as described above, the X-ray imaging apparatus 100 includes the X-ray source 2, the detector 3 configured to detect the X-rays radiated from the X-ray source 2, the medical X-ray image processing apparatus 1 configured to generate the X-ray captured image 15 from an X-ray intensity distribution detected by the detector 3, and the imaging system position changing mechanism 5 configured to change the relative position of the imaging system 7 including the X-ray source 2 and the detector 3. The medical X-ray image processing apparatus 1 is configured to acquire the positional information of the first positional reference 60a and the second positional reference 60b that appear in the plurality of X-ray captured images 15, to acquire the positional information of the imaging system 7 based on the positional information of the first positional reference 60a and the second positional reference 60b, and to evaluate the symmetry of the imaging positions of the plurality of X-ray captured images 15 with respect to the reference position 18 on the movement path SP of the imaging system 7 based on the positional information of the imaging system 7. Accordingly, it is possible to evaluate whether or not the symmetry between the actual imaging positions is ensured by evaluating the symmetry of the imaging positions of the plurality of X-ray captured images 15. Consequently, it is possible to provide the X-ray imaging apparatus 100 configured to be able to generate the reconstructed image 16 without reperforming imaging when the actual imaging positions are appropriate. In addition, it is possible to provide the X-ray imaging apparatus 100 configured to be able to significantly reduce or prevent generation of the reconstructed image 16 when the imaging positions of the plurality of X-ray captured images 15 are inappropriate from the viewpoint of the symmetry of each imaging position and the quality of the generated reconstructed image 16 is expected to deteriorate.

Second Embodiment

An X-ray imaging apparatus 200 including a medical X-ray image processing apparatus 20 according to a second embodiment of the present invention is now described with reference to FIGS. 11 to 14. In the second embodiment, the medical X-ray image processing apparatus 20 is configured to display information of imaging positions at which the symmetry is appropriate on a display 30 when the symmetry of imaging positions of a plurality of X-ray captured images 15 is inappropriate, unlike the first embodiment in which a notification for prompting image recapture is given when the symmetry of each imaging position is inappropriate. The same configurations as those of the first embodiment are denoted by the same reference numerals, and description thereof is omitted.

Figure 11:
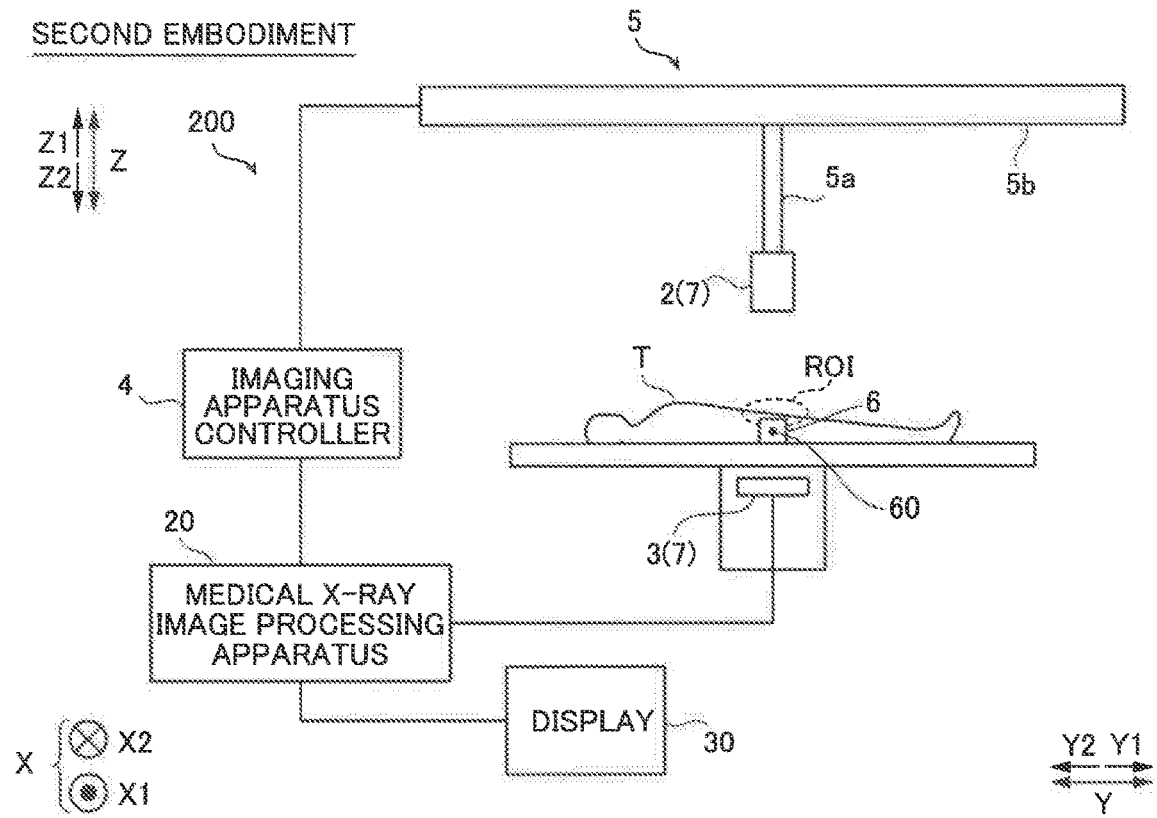
FIG. 11 is a schematic view showing the overall configuration of an X-ray imaging apparatus including a medical X-ray image processing apparatus according to a second embodiment of the present invention.

As shown in FIG. 11, the X-ray imaging apparatus 200 according to the second embodiment further includes the display 30 configured to display a display screen showing the imaging position of each of the plurality of X-ray captured images 15.

The display 30 is configured to display the display screen output from the medical X-ray image processing apparatus 20. The display 30 includes a liquid crystal monitor, for example.

Figure 12:
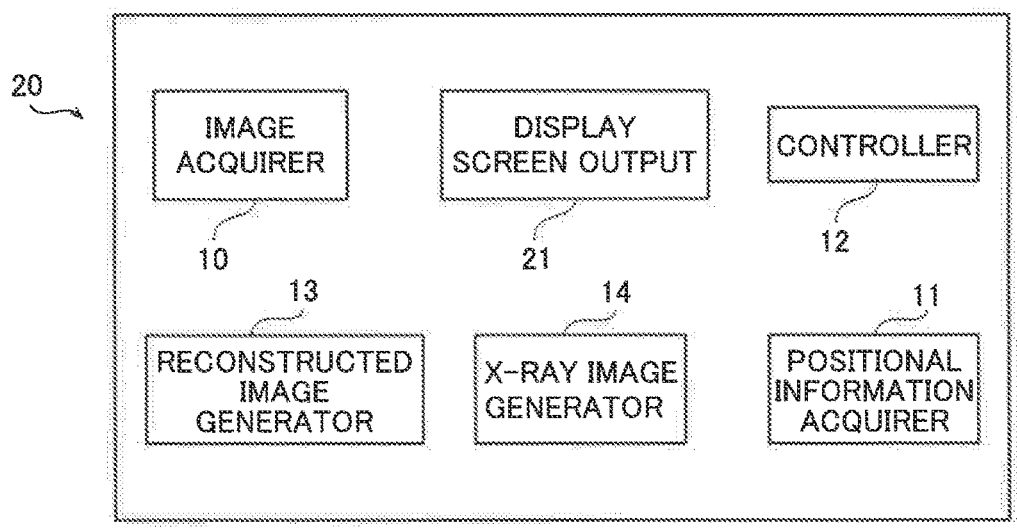
FIG. 12 is a block diagram showing the overall configuration of the medical X-ray image processing apparatus according to the second embodiment of the present invention.

As shown in FIG. 12, the medical X-ray image processing apparatus 20 according to the second embodiment further includes a display screen output 21 configured to output the display screen showing the imaging position of each of the plurality of X-ray captured images 15. The display screen output 21 is configured to output the display screen showing the imaging position of each of the plurality of X-ray captured images 15 to the display 30 based on a signal from a controller 12. The display screen output 21 is also configured to display the information of the imaging positions at which the symmetry is appropriate on the display screen based on signals from the controller 12 when the controller 12 determines that the symmetry of the imaging positions of the plurality of X-ray captured images 15 is inappropriate. The display screen output 21 is a so-called input-output interface.

The controller 12 according to the second embodiment is configured to output the display screen showing the imaging position of each of the plurality of X-ray captured images 15. In addition, the controller 12 according to the second embodiment is configured to display the information of the imaging positions at which the symmetry is appropriate on the display screen when the symmetry of the imaging positions of the plurality of X-ray captured images 15 is inappropriate.

Figure 13:
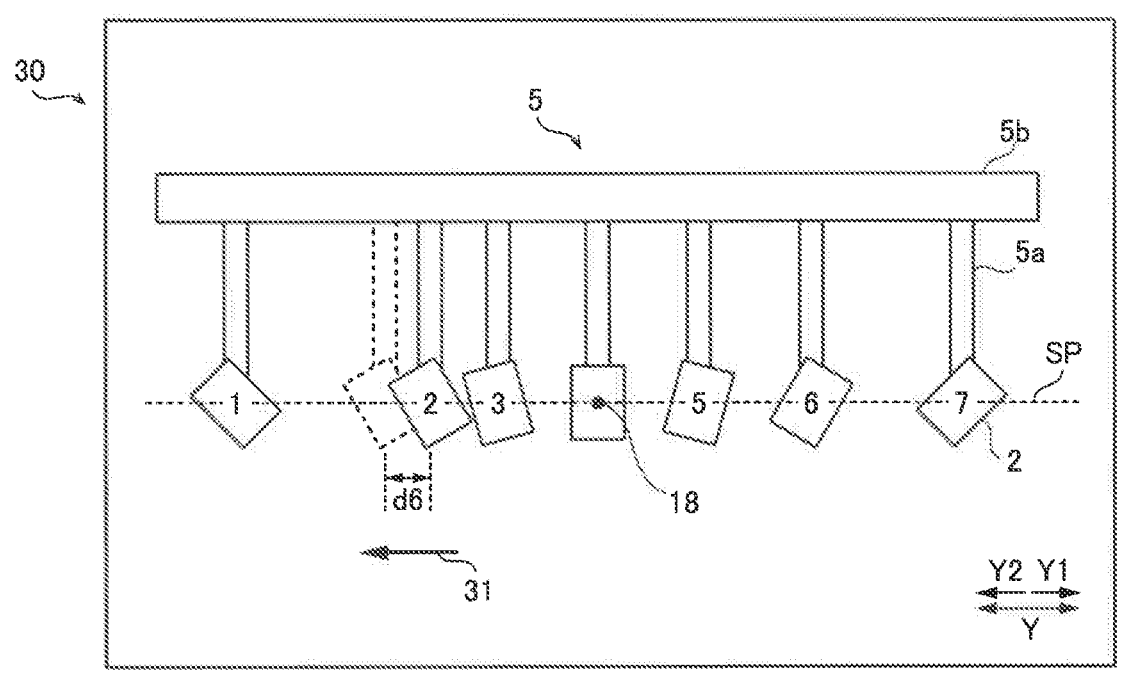
FIG. 13 is a schematic view of a display screen output from the medical X-ray image processing apparatus according to the second embodiment of the present invention.

FIG. 13 is a schematic view of the display screen displayed on the display 30. In an example shown in FIG. 13, an X-ray source 2 at each imaging position is shown by a solid line. In the example shown in FIG. 13, a second relative position is shifted in a Y1 direction, and thus the symmetry of each imaging position is inappropriate. Therefore, a position at which the symmetry of each imaging position is appropriate is shown by a one-dot chain line. Furthermore, as the information of the imaging position at which the symmetry of each imaging position is appropriate, a moving direction in which the X-ray source 2 is moved to the appropriate position is shown by an arrow 31, and a moving distance d6 to the appropriate position is shown. An operator moves an imaging system 7 based on the information of the imaging position, at which the symmetry of each imaging position is appropriate, displayed on the display 30, and reperforms imaging such that the symmetry of each imaging position is ensured. The symmetry of each imaging position is ensured such that a reconstructed image 16 is generated.

Figure 14:
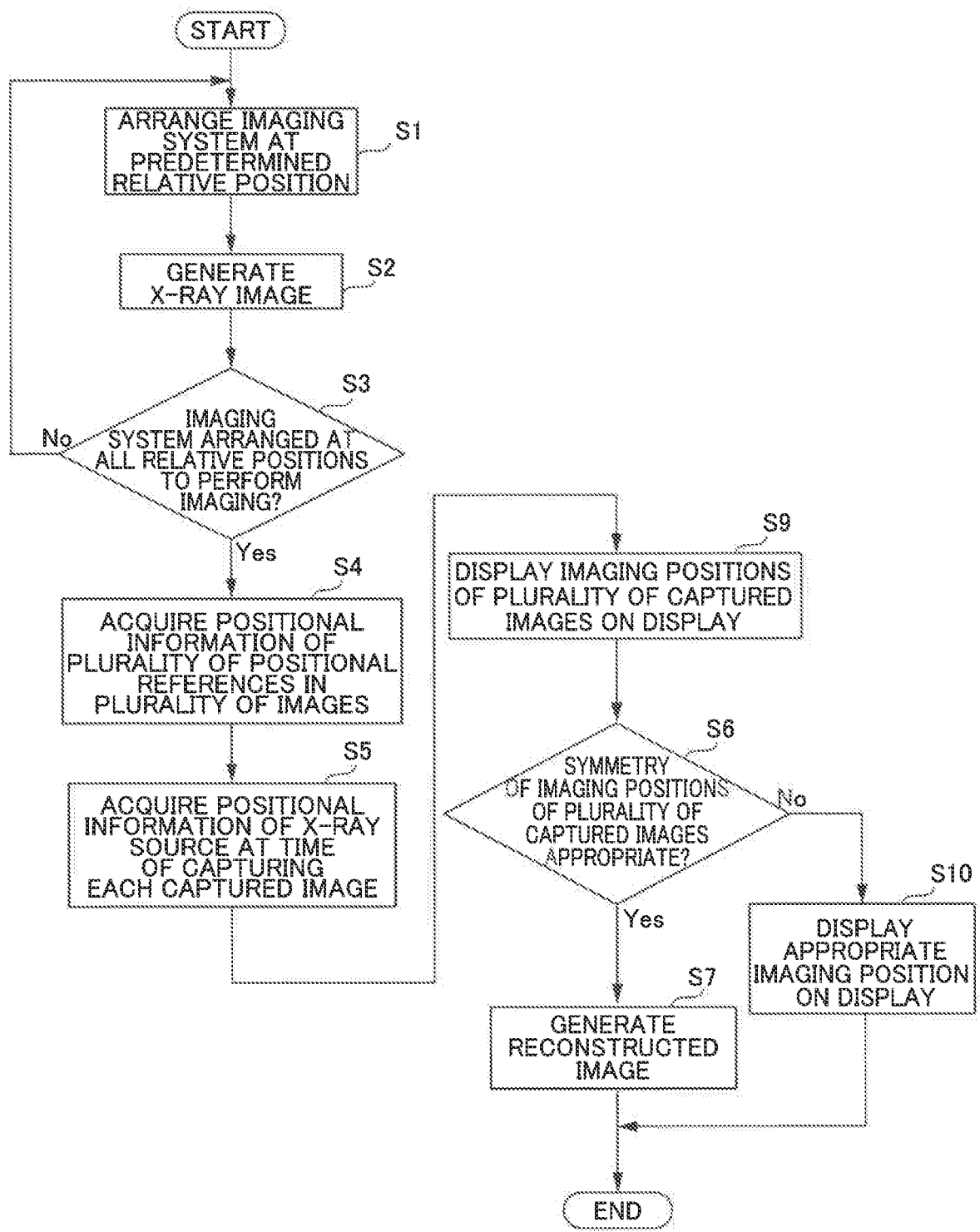
FIG. 14 is a flowchart for illustrating processing of evaluating the symmetry of imaging positions in the medical X-ray image processing apparatus according to the second embodiment of the present invention.

Processing in which the medical X-ray image processing apparatus 20 according to the second embodiment evaluates the symmetry of each imaging position is now described with reference to FIG. 14. The same processing operations as those of the first embodiment are denoted by the same reference numerals, and description thereof is omitted.

In step S1 to step S5, the imaging system 7 is arranged at all relative positions to perform imaging, the plurality of X-ray captured images 15 are generated, and positional information of the X-ray source 2 at the time of capturing each captured image is acquired. Thereafter, the processing advances to step S9.

In step S9, the controller 12 outputs the display screen showing the imaging positions of the plurality of X-ray captured images 15 to the display 30. Thereafter, the processing advances to step S6.

In step S6, the controller 12 evaluates the symmetry of each imaging position. When the symmetry of each imaging position is appropriate, the processing advances to step S7. When the symmetry of each imaging position is inappropriate, the processing advances to step S10.

In step S10, the controller 12 displays the information of the imaging positions at which the symmetry of the imaging positions of the plurality of X-ray captured images 15 is appropriate on the display screen.

The remaining configurations of the second embodiment are similar to those of the aforementioned first embodiment.

Advantages of Second Embodiment

In the second embodiment, the following advantages are obtained.

In the second embodiment, as described above, the controller 12 is configured to output the display screen showing the imaging positions of the plurality of X-ray captured images 15. Accordingly, the display screen output from the medical X-ray image processing apparatus 20 is displayed on the display 30 such that the operator can grasp each imaging position. Consequently, the operator can visually grasp the symmetry of each imaging position.

In the second embodiment, as described above, the controller 12 is configured to display the information of the imaging positions at which the symmetry is appropriate on the display screen when the symmetry of the imaging positions of the plurality of X-ray captured images 15 is inappropriate. Accordingly, the operator can grasp the positions at which the symmetry is appropriate. Consequently, it is possible to easily reperform imaging at an appropriate (symmetrical) imaging position by perform imaging based on the information of the imaging positions displayed on the display screen.

The remaining advantages of the second embodiment are similar to those of the aforementioned first embodiment.

Modified Examples

The embodiments disclosed this time must be considered as illustrative in all points and not restrictive. The scope of the present invention is not shown by the above description of the embodiments but by the scope of claims for patent, and all modifications (modified examples) within the meaning and scope equivalent to the scope of claims for patent are further included.

For example, while the example in which the medical X-ray image processing apparatus 1 sets the virtual center 18 based on the plurality of imaging positions and the region of interest ROI of the subject T has been shown in each of the aforementioned first and second embodiments, the present invention is not limited to this. For example, the controller 12 may be configured to set the virtual center 18 upon receiving an operator's setting operation.

Figure 15:
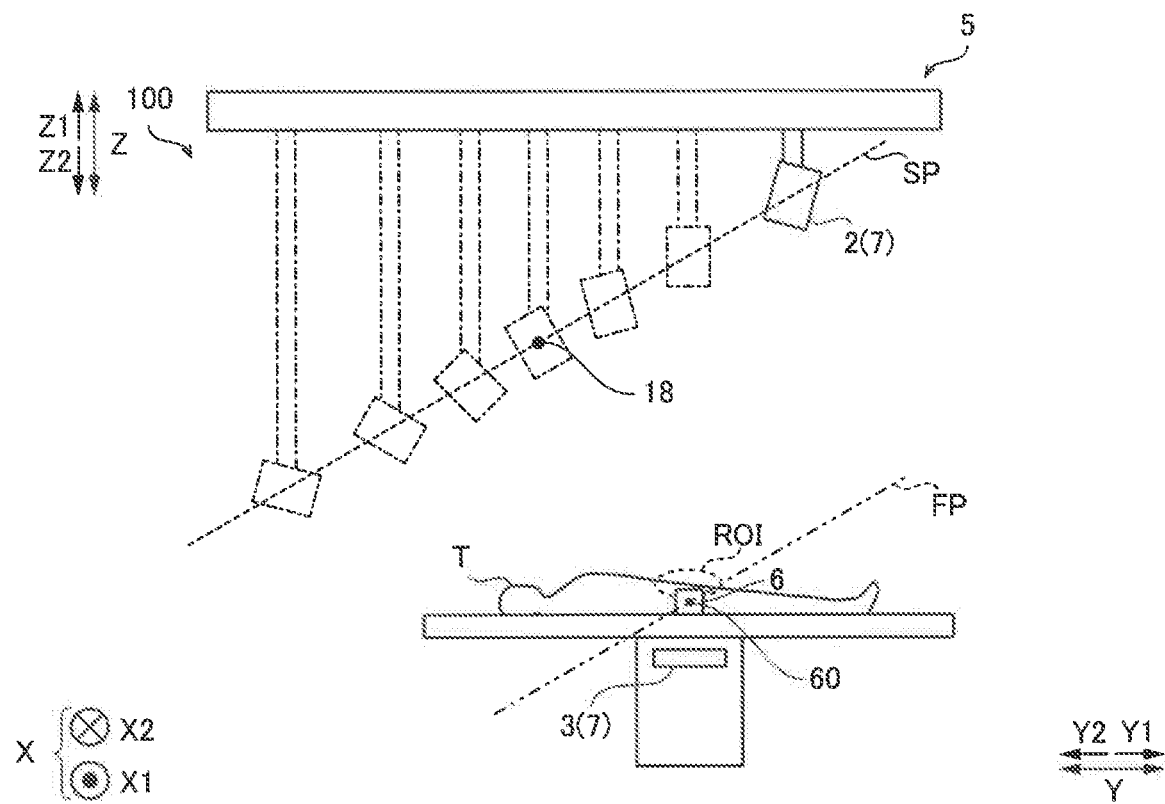
FIG. 15 is a schematic view for illustrating an imaging method in an X-ray imaging apparatus according to a first modified example of the first embodiment of the present invention.

While the example in which imaging is performed while the X-ray source 2 is moved in the Y1 direction has been shown in each of the aforementioned first and second embodiments, the present invention is not limited to this. For example, as shown in FIG. 15, imaging may be performed while the X-ray source 2 is moved in an oblique direction. When imaging is performed while the X-ray source 2 is moved in the oblique direction, a point at which the movement path SP of the X-ray source 2 and a straight line in the normal direction of the movement path SP of the X-ray source 2, which passes through the region of interest ROI of the subject T, intersect with each other may be set as the virtual center 18. With this configuration, a tomographic image of the region of interest ROI of the subject T in the direction of a straight line FP parallel to the movement path SP of the X-ray source 2 can be acquired.

While the example in which the coordinate values of the X, Y, and Z coordinates are used as the positional information of the imaging system 7 has been shown in each of the aforementioned embodiments, the present invention is not limited to this. For example, the coordinate value of the Z coordinate and the X-ray irradiation angle with respect to the detector 3 may be used as the positional information of the imaging system 7. When the X-ray irradiation angle is used as the positional information of the imaging system 7, the controller 12 may evaluate the symmetry of each imaging position by evaluating the symmetry of the irradiation angle at each imaging position using the irradiation angle from the virtual center 18 to the region of interest ROI of the subject T as a reference. In other words, the irradiation angle at the relative position that is the front position of the region of interest ROI of the subject T may be set to a reference angle (0 degrees), and the controller 12 may evaluate the symmetry of the irradiation angle with respect to the reference angle. Specifically, the controller 12 may evaluate that symmetry between the imaging positions is ensured when imaging is performed at irradiation angles of 10, 20, −10, and −20 degrees with respect to the reference angle.

While the configuration in which the imaging system 7 is automatically moved by the imaging apparatus controller 4 has been shown in each of the aforementioned first and second embodiments, the present invention is not limited to this. For example, the imaging system 7 may be manually moved by the operator such as a doctor or a technician.

While the example in which the medical X-ray image processing apparatus 1 is provided separately from the imaging apparatus controller 4 of the X-ray imaging apparatus 100 has been shown in each of the aforementioned embodiments, the present invention is not limited to this. For example, the medical X-ray image processing apparatus 1 and the imaging apparatus controller 4 may be provided integrally. That is, the imaging apparatus controller 4 of the X-ray imaging apparatus 100 may be configured to have the function of the medical X-ray image processing apparatus 1.

While the example in which the reconstructed image generator 13 generates the reconstructed image 16 using the seven X-ray captured images 15 has been shown in each of the aforementioned embodiments, the present invention is not limited to this. As long as the reconstructed image 16 can be generated, any number of X-ray captured images 15 may be used.

While the example in which the imaging system position changing mechanism 5 changes the relative position of the imaging system 7 with respect to the subject T by moving and rotating the X-ray source 2 has been shown in each of the aforementioned embodiments, the present invention is not limited to this. As long as the relative position of the imaging system 7 with respect to the subject T can be changed, either the X-ray source 2 or the detector 3 may be moved. Alternatively, the relative position of the imaging system 7 with respect to the subject T may be changed by moving both the X-ray source 2 and the detector 3.

While the example in which the positional information acquirer 11 acquires the coordinate values in the X-ray captured image 15 as the positional information of the positional references 60 has been shown in each of the aforementioned embodiments, the present invention is not limited to this. For example, the positional information acquirer 11 may be configured to acquire, as positional information, a vector value having a distance and a direction from a reference with a certain point in the X-captured ray image 15 as the reference.

While the example in which the medical X-ray image processing apparatus 1 includes the X-ray captured image generator 14 has been shown in each of the aforementioned embodiments, the present invention is not limited to this. For example, the X-ray captured image generator 14 may be provided separately from the medical X-ray image processing apparatus 1. In this case, the only requirement is that the image acquirer 10 of the medical X-ray image processing apparatus 1 be configured to acquire the X-ray captured image 15 generated in advance by the X-ray captured image generator 14 provided in the detector 3 or the like, for example.

While the example in which imaging is performed while the imaging system 7 is moved in the longitudinal direction of the subject T has been shown in each of the aforementioned embodiments, the present invention is not limited to this. For example, imaging may be performed while the imaging system 7 is moved in the short-side direction of the subject T.

While the example in which the number of captured images (imaging positions) is an odd number has been shown in each of the aforementioned embodiments, the present invention is not limited to this. The number of captured images may be an even number. As long as the imaging positions are symmetrically arranged using the reference position 18 as a reference, the number of captured images (imaging positions) may be any number.

While the example in which imaging is performed at the front position of the region of interest ROI of the subject T has been shown in each of the aforementioned embodiments, the present invention is not limited to this. It is not necessary to perform imaging at the front position of the region of interest ROI of the subject T. In this case, the controller 12 may be configured to set an intermediate point between the imaging positions at opposite ends as the virtual center 18, for example.

While the example in which on the display screen, each imaging position and the position at which the symmetry of each imaging position is appropriate are displayed as a diagram has been shown in the aforementioned second embodiment, the present invention is not limited to this. For example, the position coordinates of each imaging position and information of the imaging position at which the symmetry of each imaging position is appropriate may be displayed as numerical values.

DESCRIPTION OF REFERENCE NUMERALS 1, 20: medical X-ray image processing apparatus (image processor)
2: X-ray source
3: detector
5: imaging system position changing mechanism
6: phantom
7: imaging system
10: image acquirer
11: positional information acquirer
12: body movement information acquirer
13: reconstructed image generator
15, 15a, 15b, 15c: X-ray captured image
16: reconstructed image
18: reference position (virtual center)
19: virtual imaging position
60, 60a, 60b: positional reference
100, 200: X-ray imaging apparatus
ROI: region of interest of a subject
SP: movement path of an imaging system
T: subject

The invention claimed is:
1. A medical X-ray image processing apparatus used in an X-ray imaging apparatus configured to perform tomosynthesis in which a tomographic image parallel to a moving direction of an imaging system is generated, the medical X-ray image processing apparatus comprising:
an image acquirer configured to acquire a plurality of X-ray captured images obtained by X-ray imaging;
a positional information acquirer configured to acquire positional information of a plurality of positional references that appear in the plurality of X-ray captured images;

a reconstructed image generator configured to generate a reconstructed image obtained by reconstructing the plurality of X-ray captured images into one image; and a controller configured to acquire positional information of the imaging system based on the positional information of the plurality of positional references acquired by the positional information acquirer; wherein the controller is configured to evaluate symmetry of imaging positions of the plurality of X-ray captured images with respect to a reference position on a movement path of the imaging system based on the positional information of the imaging system.

2. The medical X-ray image processing apparatus according to claim 1, wherein the controller is configured to evaluate whether or not the reconstructed image is generated based on the symmetry of the imaging positions of the plurality of X-ray captured images.

3. The medical X-ray image processing apparatus according to claim 1, wherein the reconstructed image generator is configured to generate the reconstructed image when the controller determines that the symmetry of the imaging positions of the plurality of X-ray captured images is appropriate; and the controller is configured to give a notification for prompting recapture of an X-ray captured image captured at an inappropriate position when determining that the symmetry of the imaging positions of the plurality of X-ray captured images is inappropriate.

4. The medical X-ray image processing apparatus according to claim 1, wherein the positional information acquirer is configured to acquire the positional information of the plurality of positional references in the X-ray captured images, the plurality of positional references being provided in a phantom arranged in such a manner that the phantom together with a region of interest of a subject appears in each of the X-ray captured images.

5. The medical X-ray image processing apparatus according to claim 1, wherein the controller is configured to set a virtual center that is a front position of a region of interest of a subject on the movement path and evaluate the symmetry of the imaging positions using the virtual center, which has been set, as a reference when evaluating the symmetry of the imaging positions of the plurality of X-ray captured images.

6. The medical X-ray image processing apparatus according to claim 5, wherein the controller is configured to set the virtual center at least upon receiving an operator's setting operation or based on each of the imaging positions and the region of interest of the subject.

7. The medical X-ray image processing apparatus according to claim 5, wherein the controller is configured to evaluate the symmetry of the imaging positions of the plurality of X-ray captured images by evaluating whether or not the imaging system is arranged at each of a plurality of virtual imaging positions set symmetrically based on the virtual center.

8. The medical X-ray image processing apparatus according to claim 1, wherein the controller is configured to output a display screen showing the imaging positions of the plurality of X-ray captured images.

9. The medical X-ray image processing apparatus according to claim 8, wherein the controller is configured to display, on the display screen, information of the imaging positions at which the symmetry of the imaging positions of the plurality of X-ray captured images is appropriate when the symmetry is inappropriate.

10. The medical X-ray image processing apparatus according to claim 1, wherein the imaging system includes an X-ray source, a detector, and an imaging system position changing mechanism configured to change a relative position between the X-ray source and the detector; and the controller is configured to acquire positional information of the X-ray source based on a distance from the X-ray source to the detector, distances of the plurality of positional references from the detector, and the positional information of the plurality of positional references in the plurality of X-ray captured images.

11. An X-ray imaging apparatus comprising:

an X-ray source;

a detector configured to detect X-rays radiated from the X-ray source;

an image processor configured to generate an X-ray captured image from an X-ray intensity distribution detected by the detector; and an imaging system position changing mechanism configured to change a relative position of an imaging system including the X-ray source and the detector; wherein the image processor is configured to:

acquire positional information of a plurality of positional references that appear in a plurality of X-ray captured images;

acquire positional information of the imaging system based on the positional information of the plurality of positional references; and evaluate symmetry of imaging positions of the plurality of X-ray captured images with respect to a reference position on a movement path of the imaging system based on the positional information of the imaging system.

* * * * *